US007371844B2

(12) United States Patent
Gardella et al.

(10) Patent No.: US 7,371,844 B2
(45) Date of Patent: May 13, 2008

(54) NUCLEIC ACIDS ENCODING PARATHYROID HORMONE (PTH) DERIVATIVES

(75) Inventors: Thomas J. Gardella, Needham, MA (US); Henry M. Kronenberg, Belmont, MA (US); John T. Potts, Jr., Newton, MA (US); Harald Juppner, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/176,735

(22) Filed: Jul. 8, 2005

(65) Prior Publication Data
US 2005/0272660 A1 Dec. 8, 2005

Related U.S. Application Data

(62) Division of application No. 09/672,020, filed on Sep. 29, 2000, now Pat. No. 7,022,815.

(60) Provisional application No. 60/185,060, filed on Feb. 25, 2000, provisional application No. 60/156,927, filed on Sep. 29, 1999.

(30) Foreign Application Priority Data

Feb. 25, 2000 (WO) ..................... PCT/US00/04716

(51) Int. Cl.
*C07H 21/04* (2006.01)
*C07H 21/02* (2006.01)
*C12P 21/06* (2006.01)
*C12N 15/00* (2006.01)
*C12N 5/00* (2006.01)

(52) U.S. Cl. .................... 536/23.5; 536/23.1; 435/69.1; 435/320.1; 435/252.3; 435/325

(58) Field of Classification Search ............... 536/23.1, 536/23.5; 435/69.1, 320.1, 252.3, 254, 325, 435/254.1
See application file for complete search history.

(56) References Cited

U.S. PATENT DOCUMENTS

| | | | |
|---|---|---|---|
| 4,086,196 | A | 4/1978 | Tregear |
| 4,698,328 | A | 10/1987 | Neer et al. |
| 4,736,866 | A | 4/1988 | Leder et al. |
| 4,761,406 | A | 8/1988 | Flora et al. |
| 5,393,869 | A | 2/1995 | Nakagawa et al. |
| 5,501,979 | A | 3/1996 | Geller et al. |
| 5,656,465 | A | 8/1997 | Panicali et al. |
| 5,693,616 | A | 12/1997 | Krstenansky et al. |
| 5,723,577 | A | 3/1998 | Dong |
| 5,741,486 | A | 4/1998 | Pathak et al. |
| 5,763,416 | A | 6/1998 | Bonadio et al. |
| 5,836,905 | A | 11/1998 | Lemelson et al. |
| 5,917,123 | A | 6/1999 | McTiernan et al. |
| 5,922,927 | A | 7/1999 | Bujard et al. |

FOREIGN PATENT DOCUMENTS

| | | |
|---|---|---|
| EP | 0 477 885 A2 | 4/1992 |
| EP | 0 561 412 A1 | 9/1993 |
| EP | 0 748 817 A2 | 12/1996 |
| WO | WO 92/17581 A1 | 10/1992 |
| WO | WO 95/11988 A1 | 5/1995 |
| WO | WO 97/02834 A1 | 1/1997 |
| WO | WO 00/31266 A1 | 6/2000 |

OTHER PUBLICATIONS

Heinrich et al. "Gene encoding parathyroid hormone," J. of Biol. Chem., vol. 259, No. 5, pp. 3320-3329, Mar. 10, 1984.*
Heinrich et al. "Rat parathyroid hormone gene, exons II and III," Alignment result 8, SEQ ID No. 1, Database: GenEmbl, Accession No. K01268, Apr. 27, 1993.*
Altschul, S.F., et al., "Basic Local Alignment Search Tool," *J. Mol. Biol.* 215:403-410, Academic Press (1990).
Azarani, A., et al., "Structurally Diverse N-terminal Peptides of Parathyroid Hormone (PTH) and PTH-related Peptide (PTHRP) Inhibit the Na +/H+ Exchanger NHE3 Isoform by Binding to the PTH/PTHRP Receptor Type I and Activating Distinct Signaling Pathways," *J. Biol. Chem.* 271:14931-14936, American Society for Biochemistry and Molecular Biology (1996).
Barbier, J.-R., et al., "Bioactivities and Secondary Structures of Constrained Analogues of Human Parathyroid Hormone: Cyclic Lactams of the Receptor Binding Region," *J. Med. Chem.* 40:1373-1380, The American Chemical Society (1997).
Bisello, A., et al., "Parathyroid Hormone-Receptor Interactions Identified Directly by Photocross-linking and Molecular Modeling Studies," *J. Biol. Chem.* 273:22498-22505, American Society for Biochemistry and Molecular Biology (Aug. 1998).
Born, W., et al., "Inhibition of Parathyroid Hormone Bioactivity by Human Parathyroid Hormone (PTH)-(3-84) and PTH-(8-84) Synthesized in *Escherichia coli,* " *Endocrinol.* 123:1848-1853, The Endocrine Society (1988).
Broadus, A.E., and Stewart, A.F., "Parathyroid Hormone-Related Protein: Structure, Processing and Physiological Actions," in *The Parathyroids, Basic and Clinical Concepts,* Bilezikian, J.P., et al., eds., Raven Press, N.Y., pp. 259-294 (1994).

(Continued)

*Primary Examiner*—Jon Weber
*Assistant Examiner*—Rita Mitra
(74) *Attorney, Agent, or Firm*—Sterne, Kessler, Goldstein & Fox

(57) ABSTRACT

Parathyroid hormone(PTH) polypeptide derivatives are disclosed, as are pharmaceutical compositions containing said polypeptides, and synthetic and recombinant methods for producing said polypeptides. Also disclosed are methods for treating mammalian conditions characterized by decreases in bone mass using therapeutically effective pharmaceutical compositions containing said polypeptides. Also disclosed are methods for screening candidate compounds of the invention for antagonistic or agonistic effects on parathyroid hormone receptor action. Also disclosed are diagnostic and therapeutic methods of said compounds.

8 Claims, 13 Drawing Sheets

OTHER PUBLICATIONS

Caulfield, M.P., et al., "The Bovine Renal Parathyroid Hormone (PTH) Receptor Has Equal Affinity for Two Different Amino Acid Sequences: The Receptor Binding Domains of PTH and PTH-Related Protein Are Located within the 14-34 Region," *Endocrinol.* 127:83-87, The Endocrine Society (1990).

Cenatiempo, Y., "Prokaryotic gene expression in vitro transcription—translation coupled systems," *Biochimie* 68:505-515, Elsevier (1986).

Chorev, M., et al., "Modifications of Position 12 in Parathyroid Hormone and Parathyroid Hormone Related Protein: Toward the Design of Highly Potent Antagonists," *Biochem.* 29:1580-1586, The American Chemical Society (1990).

Cohen, F.E., et al., "Analogues of Parathyroid Hormone Modified at Positions 3 and 6," *J. Biol. Chem.* 266:1997-2004, American Society for Biochemistry and Molecular Biology (1991).

Cwirla, S. E., et al., "Peptide Agonist of the Thrombopoetin Receptor as Potent as the Natural Cytokine," *Science* 276:1696-1699, American Association for the Advancement of Science (1997).

Dong, M., et al., "Demonstration of a Direct Interaction between Residue 22 in the Carboxyl-terminal Half of Secretin and the Amino-terminal Tail of the Secretin Receptor Using Photoaffinity Labeling," *J. Biol. Chem.* 274:903-909, American Society for Biochemistry and Molecular Biology (Jan. 1999).

Fairwell, T., et al., "Total Solid-Phase Synthesis, Purification, and Characterization of Human Parathyroid Hormone-(1-84)," *Biochem.* 22:2691-2697, The American Chemical Society (1983).

Gardella, T.J., et al., "Expression of Human Parathyroid Hormone-(1-84) in *Escherichia coli* as a Factor X-cleavable Fusion Protein," *J. Biol. Chem.* 265:15854-15859, American Society for Biochemistry and Molecular Biology (1990).

Gardella, T.J., et al., "Mutational Analysis of the Receptor-activating Region of Human Parathyroid Hormone," *J. Biol. Chem.* 266:13141-13146, American Society for Biochemistry and Molecular Biology (1991).

Gardella, T.J., et al., "Analysis of Parathyroid Hormone's Principal Receptor-Binding Region by Site-Directed Mutagenesis and Analog Design," *Endocrinol.* 132:2024-2030, The Endocrine Society (1993).

Gardella, T.J., et al., "Parathyroid Hormone (PTH)-PTH-related Peptide Hybrid Peptides Reveal Functional Interations between 1-14 and 15-34 Domains of the Ligand," *J. Biol. Chem.* 270:6584-6588, American Society for Biochemistry and Molecular Biology (1995).

Goltzmann, D., et al., "Analysis of the Requirements for Parathyroid Hormone Action in Renal Membranes with the Use of Inhibiting Analogues," *J. Biol. Chem.* 250:3199-3203, American Society for Biochemistry and Molecular Biology (1975).

Gombert, F.O., et al., "Alanine and D-Amino Acid Scan of Human Parathyroid Hormone," in *Peptides: Chemistry, Structure and Biology*, Kaumaya, P.T.P. and Hodges, R.S., eds., Mayflower Scientific Ltd., England, UK, pp. 661-662 (1996).

Gottesman, S., "Bacterial Regulation: Global Regulatory Networks," *Ann. Rev. Genet.* 18:415-441, Annual Reviews, Inc. (1984).

Goud, N.A., et al., Solid-Phase Synthesis and Biologic Activity of Human Parathyroid Hormone(1-84), *J. Bone Min. Res.* 6:781-789, Mary Ann Liebert, Inc. (1991).

Hoare, S.R.J., et al., "Measurement of Agonist and Antagonist Ligand-Binding Parameters at the Human Parathyroid Hormone Type 1 Receptor: Evaluation of Receptor States and Modulation by Guanine Nucleotide," *J. Pharmacol. Exp. Ther.* 289:1323-1333, American Society for Pharmacology and Experimental Therapeutics (Jun. 1999).

Holtmann, M.H., et al., "Critical Contributions of Amino-terminal Extracellular Domains in Agonist Biding and Activation of Secretin and Vasoactive Intestinal Polypeptide Receptors," *J. Biol. Chem.* 270:14394-14398, American Society for Biochemistry and Molecular Biology (1995).

Holtmann, M. H., et al., "Molecular Basis and Species Specificity of High Affinity Binding of Vasoactive Intestinal Polypeptide by the Rat Secretin Receptor," *J. Pharmacol. Exp. Ther.* 279:555-560, American Society for Pharmacology and Experimental Therapeutics (1996).

Horiuchi, N., et al., "A Parathyroid Hormone Inhibitor in vivo: Design and Biological Evaluation of a Hormone Analog," *Science* 220:1053-1055, American Association for the Advancement of Science (1983).

Izaki, K., "Plasmid Induced Heavy Metal Resistance in Bacteria," *Jpn. J. Bacteriol.* 33:729-742, Japanese Society for Bacteriology (1978) [in Japanese].

John, Jr., J.F., and Twitty, J.A., "Plasmids as Epidemiologic Markers in Nosocomial Gram-Negative Bacilli: Experience at a University and Review of the Literature," *Rev. Infect. Dis.* 8:693-704, The University of Chicago Press (1986).

Jüppner, H., et al., "The Parathyroid Hormone-like Peptide Associated with Humoral Hypercalcemia of Malignancy and Parathyroid Hormone Bind to the Same Receptor on the Plasma Membrane of ROS 17/2.8 cells," *J. Biol. Chem.* 263:8557-8560, American Society for Biochemistry and Molecular Biology (1988).

Jüppner, H., et al., "Properties of Amino-Terminal Parathyroid Hormone-Related Peptides Modified at Positions 11-13," *Peptides* 11:1139-1142, Pergamon Press (1990).

Jüppner, H., et al., "A G Protein-Linked Receptor for Parathyroid Hormone and Parathyroid Hormone-Related Peptide," *Science* 254:1024-1026, American Association for the Advancement of Science (1991).

Karaplis, A.C., et al., "Lethal skeletal dysplasia from targeted disruption of the parathyroid hormone-related peptide gene," *Genes & Develop.* 8:277-289, Cold Spring Harbor Laboratory Press (1994).

Kimura, T., et al., "Discovery of a Novel Thrombopoietin Mimic Agonist Peptide," *J. Biochem.* 122:1046-1051, The Japanese Biochemistry Society (1997).

Kotin, R.M., et al., "Site-specific integration by adeno-associated virus," *Proc. Natl. Acad.. Sci. USA* 87:2211-2215, National Academy of Sciences of the USA (1990).

Kronenberg, H.M., et al., "Parathyroid Hormone: Biosynthesis, Secretion, Chemistry and Action," in *Handbook of Experimental Pharmacology*, vol. 107, Mundy, G.R. and Martin, T.J., eds., Springer-Verlag, NY, pp. 507-567 (1993).

Kronenberg, H.M., et al., "The PTH/PTHrP Receptor: One Receptor for Two Ligands," in *Molecular Genetics of Endocrine Disorders*, Thakker, R.V., ed., Chapman & Hall Medical, London, UK, pp. 389-420 (1997).

Lanske, B., et al., "PTH/PTHrP Receptor in Early Development and Indian Hedgehog-Regulated Bone Growth," *Science* 273: 663-666, American Association for the Advancement of Science (1996).

Lebkowski, J.S., et al., "Adeno-Associated Virus: a Vector System for Efficient Introduction and Integration of DNA into a Variety of Mammalian Cell Types," *Mol. Cell. Biol.* 8:3988-3996, The American Society for Microbiology (1988).

Li, B., et al., "Minimization of a Polypeptide Hormone," *Science* 270:1657-1660, American Association for the Advancement of Science (1995).

Livnah, O., et al., "Functional Mimicry of a Protein Hormone by a Peptide Agonist: The EPO Receptor Complex at 2.8Å," *Science* 273:464-471, American Association for the Advancement of Science (1996).

Luck, M.D., et al., "The (1-14) Fragment of Parathyroid Hormone (PTH) Activates Intact and Amino-Terminally Truncated PTH-1 Receptors," *Molecular Endocrinol.* 13:670-680, The Endocrine Society (May 1999).

Majeska, R. J., et al., "Parathyroid Hormone-Responsive Clonal Cell Lines from Rat Osteosarcoma," *Endocrinol.* 107:1494-1503, The Endocrine Society (1980).

Mannstadt, M., et al., "Evidence for a Ligand Interaction Site at the Amino-Terminus of the Parathyroid Hormone (PTH)/PTH-related Protein Receptor from Cross-linking and Mutational Studies," *J. Biol. Chem.* 273:16890-16896, American Society for Biochemistry and Molecular Biology (Jul. 1998).

Neugebauer, W., et al., "Solution Structure and Adenylyl Cyclase Stimulating Activities of C-Terminal Truncated Human Parathyroid Hormone Analogues," *Biochem.* 34:8835-8842 (1995).

Nissenson, R.A., et al., "Synthetic Peptides Comprising the Amino-terminal Sequence of a Parathyroid Hormone-like Protein from Human Malignancies," *J. Biol. Chem.* 263:12866-12871, American Society for Biochemistry and Molecular Biology (1988).

Nussbaum, S. R., et al., "Parathyroid Hormone γ Renal Receptor Interactions," *J. Biol. Chem.* 255:10183-10187, American Society for Biochemistry and Molecular Biology (1980).

Plotkin, H., et al., "Dissociation of Bone Formation from Resorption during 2-Week Treatment with Human Parathyroid Hormone-Related Peptide-(1-36) in Humans: Potential as an Anabolic Therapy for Osteoporosis," *J. Clin. Endocrinol. & Metabol.* 83:2786-2791, The Endocrine Society (Aug. 1998).

Potts, J.T., et al., "Structure based design of parathyroid hormone analogs," *J. Endocrinol.* 154:S15-S21, A Society for Endocrinology Publication (1997).

Rixon, R.H., et al., "Parathyroid Hormone Fragments May Stimulate Bone Growth in Ovariectomized Rats by Activating Adenylyl Cyclase," *J. Bone Miner. Res.* 91179-1189, Mary Ann Liebert, Inc. (1994).

Roe, E.B., et al., "Parathyroid Hormone 1-34 (hPTH 1-34) and Estrogen Produce Dramatic Bone Density Increases in Postmenopausal Osteoporposis—Results from a Placebo-Controlled Randomized Trial," *J. Bone & Mineral Res.* 14:S137, Abstract No. 1019, Blackwell Science, Inc. (Sep. 1999).

Rosenblatt, M., et al., "Identification of a Receptor-Binding Region in Parathyroid Hormone," *Endocrinol.* 107:545-550, The Endocrine Society (1980).

Rosenblatt, M., "Parathyroid Hormone: Chemistry and Structure-Activity Relations," in *Pathobiology Annual*, vol. 11, Ioachim, H.L., ed., Raven Press, N.Y., pp. 53-86 (1981).

Schipani, E., et al., "Identical Complementary Deoxyribonucleic Acids Encode a Human Renal and Bone Parathyroid Hormone (PTH)/PTH-Related Peptide Receptor," *Endocrinol.* 132:2157-2165, The Endocrine Society (1993).

Segre, G. V., and Goldring, S. R., "Receptors for Secretin, Calcitonin, Parathyroid Hormone (PTH)/PTH-Related Peptide, Vasoactive Intestinal Peptide, Glucagonlike Peptide 1, Growth Hormone-Releasing Hormone, and Glucagon Belong to a Newly Discovered G-Protein -Linked Receptor Family," *Trends in Endo. Metab.* 4:309-314, Elsevier Science Publishing Co. (1993).

Seifter, S., and Englard, S., "Analysis for Protein Modifications and Nonprotein Cofactors," *Methods in Enzymol.* 182:626-646, Academic Press, Inc. (1990).

Shen, V., et al., "Effects of Combined and Separate Intermittent Administration of Low-Dose Human Parathyroid Hormone Fragment (1-34) and 17γ-Estradiol on Bone Histomorphometry in Ovariectomized Rats with Established Osteopenia," *Calcif. Tissue Int.* 50:214-220, Springer-Verlag New York Inc. (1992).

Shimizu, M., et al., "Type-Substitution Analysis of the Amino-Terminal Fragment of Parathyroid Hormone, PTH(1-14): An Approach toward New Low Molecular Weight PTH Agonists," *J. Bone & Miner. Res.* 14(*suppl. 1*):Abstract No. F398, Mary Ann Liebert, Inc. (Sep. 1999).

Shimizu, M., et al., "Minimization of Parathyroid Hormone," *J. Biol. Chem.* 275:21836-21843, American Society for Biochemistry and Molecular Biology (Jul. 2000).

Slovik, D.M., et al., "Restoration of Spinal Bone in Osteoporotic Men by Treatment With Human Parathyroid Hormone (1-34) and 1,25-Dihydroxyvitamin D," *J. Bone Miner. Res.* 1:377-381, Mary Ann Liebert, Inc. (1986).

Stroop, S.D., et al., "Chimeric Human Calcitonin and Glucagon Receptors Reveal Two Dissociable Calcitonin Interaction Sites," *Biochem.* 34:1050-1057, American Chemical Society (1995).

Takasu, H., et al., "Dual Signaling and Ligand Selectivity of the Human PTH/PTHrP Receptor," *J. Bone Miner. Res.* 14:11-20, American Society for Bone and Mineral Research (Jan. 1999).

Tregear, G.W., et al., "Bovine Parathyroid Hormone: Minimum Chain Length of Synthetic Peptide Required for Biological Activity," *Endocrinol.* 93:1349-1353, The Endocrine Society (1973).

Tregear, G.W., and Potts, Jr., J.T., "Synthetic Analogues of Residues 1-34 of Human Parathyroid Hormone: Influence of Residue No. 1 on Biological Potency In Vitro," *Endocrine Res. Comm.* 2:561-570, Marcel Dekker, Inc. (1975).

Ureña, P., et al., "Regulation of Parathyroid Hormone (PTH)/PTH-Related Peptide Receptor Messenger Ribonucleic Acid by Glucocorticoids and PTH in ROS 17/2.8 and OK Cells," *Endocrinol.* 134:451-456, The Endocrine Society (1994).

Usdin, T.B., et al., "Identification and Functional Expression of a Receptor Selectively Recognizing Parathyroid Hormone, the PTH2 Receptor," *J. Biol. Chem.* 270: 15455-15458, American Society for Biochemistry and Molecular Biology (1995).

Wells, J. A., "Hormone Mimicry," *Science* 273:449-450, American Association for the Advancement of Science (1996).

Whitfield, J.F., et al. "Restoration of Severely Depleted Femoral Trabecular Bone in Ovariectomized Rats by Parathyroid Hormone-(1-34)," *Calcif. Tissue Int.* 56:227-231, Springer-Verlag New York Inc. (1995).

Whitfield, J.F., and Morley, P., "Small bone-building fragments of parathyroid hormone: new therapeutic agents for osteoporosis," *Trends Pharmacol. Sci.* 16:372-376, Elsevier Science Ltd. (1995).

Whitfield, J.F., et al., "Comparison of the Ability of Recombinant Human Parathyroid Hormone, rhPTH-(1-84), and hPTH-(1-31)NH2 to Stimulate Femoral Trabecular Bone Growth in Ovariectomized Rats," *Calcif. Tissue Int.* 60:26-29, Springer-Verlag New York, Inc. (1997).

Wrighton, N.C., et al., "Small Peptides as Potent Mimetics of the Protein Hormone Erythropoietin," *Science* 273:458-463, American Association for the Advancement of Science (1996).

Dialog, English language abstract of Izaki, K., "Plasmid Induced Heavy Metal Resistance in Bacteria," *Jpn. J. Bacteriol.* 33:729-742, Japanese Society for Bacteriology (1978).

Copy of International Search Report for International Application No. PCT/US00/04716, mailed Oct. 11, 2000, European Patent Office, Netherlands.

Shimizu, M., et al., "Enhanced Activity in Parathyroid Hormone-(1-14) and -(1-11): Novel Peptides for Probing Ligand-Receptor Interactions," *Endocrinol.* 142:3068-3074, The Endocrine Society (Jul. 2001).

\* cited by examiner

NUCLEIC ACIDS ENCODING PARATHYROID HORMONE (PTH) DERIVATIVES

This application is a divisional of U.S. application Ser. No. 09/672,020, filed Sep. 29, 2000, now U.S. Pat. No. 7,022,815; which claims the benefit of U.S. Provisional Appl. No. 60/156,927, filed Sep. 29, 1999 and claims the benefit of U.S. Provisional Appl. No. 60/185,060, filed Feb. 25, 2000; each of which are incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government may have certain rights in this invention.

BACKGROUND OF THE INVENTION

1. Field of the Invention

The present invention relates to novel parathyroid hormone (PTH) polypeptide derivatives, nucleic acids encoding the PTH derivatives and methods of preparing and using the PTH derivatives.

2. Description of Related Art

Parathyroid Hormone

Parathyroid hormone (PTH) is a major regulator of calcium homeostasis whose principal target cells are found in bone and kidney. Native human parathyroid hormone is a polypeptide of 84 amino acids. It is secreted from the parathyroid glands in response to low blood calcium levels and acts on osteoblast (bone-building cells) in bone, and on tubular epithelial cells of the kidney. The hormone interacts with a cell surface receptor molecule, called the PTH-1 receptor or PTH/PTHrP receptor, which is expressed by both osteoblast and renal tubular cells. Administration of intermittent doses of PTH has potent anabolic effects on bone.

PTHrP, the major cause of the humoral hypercalcemia of malignancy, also has normal functions that include roles in development. PTHrP has 141 amino acids, although variants also occur that result from alternative gene splicing mechanisms. PTHrP plays a key role in the formation of the skeleton through a process that also involves binding to the PTH-1 receptor (Karaplis, A. C., et al., *Genes and Dev.* 8:277-289 (1994) and Lanske, B., et al., *Science* 273:663-666 (1996)).

Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH is thought to exert these effects primarily through receptor-mediated activation of adenylate cyclase and/or phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcemia, humoral hypercalcemia of malignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues. PTHrP is normally found at low levels in many tissues, including keratinocytes, brain, pituitary, parathyroid, adrenal cortex, medulla, fetal liver, osteoblast-like cells, and lactating mammary tissues. In many HHM malignancies, PTHrP is found in the circulatory system at high levels, thereby producing the elevated calcium levels associated with HHM.

The pharmacological profiles of PTH and PTHrP are nearly identical in most in vitro assay systems, and elevated blood levels of PTH (i.e., primary hyperparathyroidism) or PTHrP (i.e., HHM) have comparable effects on mineral ion homeostasis (Broadus, A. E. & Stewart, A. F., "Parathyroid hormone-related protein: Structure, processing and physiological actions," in Basic and Clinical Concepts, Bilzikian, J. P. et al., eds., Raven Press, New York (1994), pp. 259-294; Kronenberg, H. M. et al., "*Parathyroid hormone: Biosynthesis, secretion, chemistry and action*," in Handbook of Experimental Pharmacology, Mundy, G. R. & Martin, T. J., eds., Springer-Verlag, Heidelberg (1993), pp. 185-201). The similarities in the biological activities of the two ligands can be explained by their interaction with a common receptor, the PTH/PTHrP receptor, which is expressed abundantly in bone and kidney (Urena, P. et al., *Endocrinology* 134:451-456 (1994)).

PTH Receptor

The PTH-1 receptor is homologous in primary structure to a number of other receptors that bind peptide hormones, such as secretin (Ishihara, T. et al., *EMBO J.* 10:1635-1641 (1991)), calcitonin (Lin, H. Y. et al., *Science* 254:1022-1024 (1991)) and glucagon (Jelinek, L. J. et al., *Science* 259:1614-1616 (1993)); together these receptors form a distinct family called receptor family B (Kolakowski, L. F., *Receptors and Channels* 2:1-7 (1994)). Within this family, the PTH-1 receptor is unique, in that it binds two peptide ligands and thereby regulates two separate biological processes. A recently identified PTH receptor subtype, called the PTH-2 receptor, binds PTH but not PTHrP (Usdin, T., et al., *J. Biol. Chem.* 270:15455-15458 (1995)). This observation implied that structural differences in the PTH and PTHrP ligands determined selectivity for interaction with the PTH-2 receptor. The PTH-2 receptor has been detected by RNA methods in the brain, pancreas and vasculature, however, its biological function has not been determined (Usdin, T., et al., *J. Biol. Chem.* 270:15455-15458 (1995)). It is hypothesized that the family B receptors use a common molecular mechanism to engage their own cognate peptide hormone (Bergwitz, C., et al., *J. Biol. Chem.* 271:26469-26472 (1996)).

The binding of either radiolabeled PTH(1-34) or PTHrP (1-36) to the PTH-1 receptor is competitively inhibited by either unlabeled ligand (Jüppner, H. et al., *J. Biol. Chem.* 263:8557-8560 (1988); Nissenson, R. A. et al., *J. Biol. Chem.* 263:12866-12871 (1988)). Thus, the recognition sites for the two ligands in the PTH-1 receptor probably overlap. In both PTH and PTHrP, the 15-34 region contains the principal determinants for binding to the PTH-1 receptor. Although these regions show only minimal sequence homology (only 3 amino acid identities), each 15-34 peptide can block the binding of either PTH(1-34) or PTHrP(1-34) to the PTH-1 receptor (Nussbaum, S. R. et al., *J. Biol. Chem.* 255:10183-10187 (1980); Caulfield, M. P. et al., *Endocrinology* 127:83-87 (1990); Abou-Samra, A.-B. et al., *Endocrinology* 125:2215-2217 (1989)). Further, the amino terminal portion of each ligand is required for bioactivity, and these probably interact with the PTH-1 receptor in similar ways, since 8 of 13 of these residues are identical in PTH and PTHrP.

Both PTH and PTHrP bind to the PTH-1 receptor with affinity in the nM range; the ligand-occupied receptor transmits a "signal" across the cell membrane to intracellular effector enzymes through a mechanism that involves intermediary heterotrimeric GTP-binding proteins (G proteins). The primary intracellular effector enzyme activated by the PTH-1 receptor in response to PTH or PTHrP is adenyl cyclase (AC). Thus, PTH induces a robust increase in the "second messenger" molecule, cyclic adenosine monophosphate (cAMP) which goes on to regulate the poorly characterized "downstream" cellular processes involved in bone-remodeling (bone formation and bone resorption processes). In certain cell-based assay systems, PTH can stimulate effector enzymes other than AC, including phospholipase C (PLC), which results in production of inositol triphosphate ($IP_3$), diacylglycerol (DAG) and intracellular calcium ($iCa^{2+}$). The roles of various second messenger molecules in bone metabolism are presently unknown.

Osteoporosis

Osteoporosis is a potentially crippling skeletal disease observed in a substantial portion of the senior adult population, in pregnant women and even in juveniles. The term osteoporosis refers to a heterogeneous group of disorders. Clinically, osteoporosis is separated into type I and type II. Type I osteoporosis occurs predominantly in middle aged women and is associated with estrogen loss at menopause, while osteoporosis type II is associated with advancing age. Patients with osteoporosis would benefit from new therapies designed to promote fracture repair, or from therapies designed to prevent or lessen the fractures associated with the disease.

The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success. These agents act to decrease bone resorption. Since parathyroid hormone regulates blood calcium and the phosphate levels, and has potent anabolic (bone-forming) effects on the skeleton, in animals (Shen, V., et al., *Calcif. Tissue Int.* 50:214-220 (1992); Whitefild, J. F., et al., *Calcif. Tissue Int.* 56:227-231 (1995) and Whitfield, J. F., et al., *Calcif. Tissue Int.* 60:26-29 (1997)) and humans (Slovik, D. M., et al., *J. Bone Miner. Res.* 1:377-381 (1986); Dempster, D. W., et al., *Endocr. Rev.* 14:690-709 (1993) and Dempster, D. W., et al., *Endocr. Rev.* 15:261 (1994)) when administered intermittently, PTH, or PTH derivatives, are prime candidates for new and effective therapies for osteoporosis.

PTH Derivatives

PTH derivatives include polypeptides that have amino acid substitutions or are truncated relative to the full length molecule. Both a 14 and a 34 amino acid amino-terminal truncated form of PTH, as well as a C-terminal truncated form have been studied. Additionally, amino acid substitutions within the truncated polypeptides have also been investigated. Frequently, either hPTH or rPTH is referred which are respectively human or rat PTH.

Truncated PTH derivatives such as PTH(1-34) and PTH (1-31) are active in most assay systems and promote bone-formation (Whitefild, J. F., et al., *Calcif. Tissue Int.* 56:227-231 (1995); Whitfield, J. F., et al., *Calcif. Tissue Int.* 60:26-29 (1997); Slovik, D. M., et al., *J. Bone Miner. Res.* 1:377-381 (1986); Tregear, G. W., et al., *Endocrinology* 93:1349-1353 (1973); Rixon, R. H., et al., *J. Bone Miner. Res.* 9:1179-1189 (1994); Whitfield, J. F. and Morley, P., *Trends Pharmacol. Sci.* 16:372-386 (1995) and Whitfield, J. F., et al., *Calcif. Tissue Int.* 58:81-87 (1996)). But these peptides are still too large for efficient non-parenteral delivery and low cost. The discovery of an even smaller "minimized" version of PTH or PTHrP would be an important advance in the effort to develop new treatments for osteoporosis.

Smaller truncated derivatives of PTH have also been studied. This includes a PTH(1-14) fragment (Luck et al., *Mol. Endocrinol.* 13:670-80 (1999)), a PTH(1-13) fragment (Bergwitz C., et al., *J. Biol. Chem.* 271:4217-4224 (1996)). A truncated 27 amino acid PTH has also been reported. Potts, J. et al., *J. Endocrin.* 154"S 15-S21 (1997). Additional derivatives are discussed in U.S. Pat. Nos. 5,393,869; 5,723, 577; 5,693,616 and E.P. Patent No. 748817.

PTH and PTHrP derivatives that have amino acid substitutions or deletions in the 1-14 region usually exhibit diminished activity (Tregear, G. W., et al., *Endocrinology* 93:1349-1353 (1973); Goltzman, D., et al., *J. Biol. Chem.* 250:3199-3203 (1975); Horiuchi, N., et al., *Science* 220: 1053-1055 (1983) and Gardella, T. J., et al., *J. Biol. Chem.* 266:13141-13146 (1991)). Additionally, there have been studies of single amino acid substitution in large PTH fragments (Gombert, F. O. et al., *Peptide Chemistry, Structure and Biology* in Proceedings of the 14$^{th}$ American Peptide Symposium, Jun. 18-23, 1996; Cohen, F. E. et al., *J. Biol. Chem.* 266:1997-2004, 1991; Juppner, H. et al., *Peptides* 11:1139-1142, 1990).

Several short $NH_2$-terminal PTH or PTHrP peptides have been investigated previously, but no activity was detected. For example, bPTH(1-12) was inactive in adenyl cyclase assays performed in rat renal membranes (Rosenblatt, M., "Parathyroid Hormone: Chemistry and Structure-Activity Relations," in Pathobiology Annual, Ioachim, H. L., ed., Raven Press, New York (1981), pp. 53-84) and PTHrP(1-16) was inactive in AC assays performed in Chinese hamster ovary (CHO) cells expressing the cloned rat PTH-1 receptor (Azurani, A., et al., *J. Biol. Chem.* 271:14931-14936(1996)). It has been known that residues in the 15-34 domain of PTH contribute importantly to receptor binding affinity, as the PTH(15-34) fragment binds weakly to the receptor, but this peptide does not activate AC (Naussbaum, S. R., et al., *J. Biol. Chem.* 255:10183-10187 (1980) and Gardella, T. J., et al., *Endocrinology* 132:2024-2030 (1993))

It has previously been reported (Luck et al., *Mol. Endocrin.* 13 (1999)) that PTH(1-14) activates adenyl cyclase in cells expressing PTH-1 receptors, although potency was much weaker than that of PTH(1-34) ($E_c50s=100$ μM and ~1 nM respectively). Additionally, by alanine-scanning substitution analysis of PTH(1-14), it was shown that positions 3 and 10-14 are tolerant sites, whereas positions 2 and 4-9 are comparatively intolerant sites.

Additionally, further characterization of substitutions in PTH(1-14) have been reported (Shimizu, M., et al., *J. Biol. Chem.* 275: 21836-21843 (2000)). In order to further characterize the amino acids in PTH(1-14), and to potentially improve activity, a variety of single substitutions were introduced such that at least one type of amino acid (e.g. polar, apolar, cationic, small, aromatic) as well as proline was represented at each position.

Thus, this invention meets a need in the art for new PTH derivatives that can be used to treat patients in need of treatment of bone-related defects or diseases or any condition in which parthyroid hormone is involved. As such, the invention is drawn to novel truncated derivatives of PTH, including PTH(1-14), PTH(1-20), PTH(1-22), PTH(1-24), PTH(1-26), PTH(1-28), PTH(1-30), PTH(1-32), and PTH (1-34), methods of making and using the derivatives as well as methods of using the derivatives to treat patients with various bone-related defects or diseases.

SUMMARY OF THE INVENTION

The invention is drawn to, inter alia, novel PTH polypeptide derivatives containing amino acid substitutions at selected positions in the polypeptides. The derivatives may function as full, or nearly full, agonists of the PTH-1 receptor. Because of the unique properties these polypeptides have a utility as drugs for treating human diseases of the skeleton, such as osteoporosis.

The invention relates to derivatives of PTH(1-14), PTH (1-20), PTH(1-22), PTH(1-24), PTH(1-26), PTH(1-28), PTH(1-30), PTH(1-32), and PTH(1-34) polypeptides and the nucleic acids encoding those polypeptides. Fragments of the polypeptides are also part of the invention The invention further relates to compositions and methods for use in limiting undesired bone loss in a vertebrate at risk of such bone loss, in treating conditions that are characterized by undesired bone loss or by the need for bone growth, e.g. in treating fractures or cartilage disorders and for raising cAMP levels in cells where deemed necessary.

The invention is first directed to a polypeptide having the amino acid sequence consisting essentially of AlaValAlaGluIleGlnLeuMetHis$X_{01}X_{02}X_{03}$Lys$X_{04}$(SEQ ID NO:1), wherein: $X_{01}$ is Ala, Asp or Gln, $X_{02}$ is Leu, Arg or homoArg; $X_{03}$ is Arg or Ala; and $X_{04}$ is Phe or Trp. In one specific embodiment, this invention provides a polypeptide at least 90% identical to the polypeptide of SEQ ID NO:1. In another embodiment Ala-3 may be substituted with Serine. In yet another embodiment, at least one of $X_{01}X_{02}X_{03}$ or $X_{04}$ may be the native amino acid for that position, provided that not all X's are substituted so as to result in the native PTH(1-14) of either rat or human.

The invention is further directed to a polypeptide having an amino acid sequence consisting essentially of AlaValAlaGluIleGlnLeuMetHis$X_{01}$ArgAlaLys$X_{02}$(SEQ ID NO:2), wherein; $X_{01}$ is Ala or Gln; and $X_{02}$ is Trp or His. In one specific embodiment, this invention provides a poly peptide at least 85% identical to this peptide. More preferably the polypeptide is 90% identical.

In one embodiment the invention is specifically directed to a polypeptide having the following amino acid sequences:

```
                                          (SEQ ID No:3)
AlaValAlaGluIleGlnLeuMetHisAlaArgAlaLysHis, (SEQ ID No:4)
AlaValSerGluIleGlnLeuMetHisAsnArgGlyLysHis, (SEQ ID No:5)
AlaValSerGluIleGlnLeuMetHisAsnArgAlaLysHis, (SEQ ID No:6)
AlaValAlaGluIleGlnLeuMetHisAsnArgAlaLysHis, (SEQ ID No:7)
AlaValAlaGluIleGlnLeuMetHisAlaArgAlaLysTrp,
and (SEQ ID No:8)
AlaValAlaGluIleGlnLeuMetHisGlnArgAlaLysHis.
```

The invention is further drawn to specific shorter PTH derivatives having the following amino acid sequences:

```
                                          (SEQ ID No:9)
AlaValAlaGluIleGlnLeuMetHisAlaArgAlaLys, (SEQ ID No:10)
AlaValAlaGluIleGlnLeuMetHisAlaArgAla, (SEQ ID No:11)
AlaValAlaGluIleGlnLeuMetHisAlaArg,
and (SEQ ID No:13)
AlaValSerGluIleGlnLeuMetHisAlaArgAlaLysHis.
```

The invention is also drawn to longer PTH derivatives, where the first 14 amino acids have the sequence AlaValAlaGluIleGlnLeuMetHis$X_{01}X_{02}X_{03}$Lys$X_{04}$ (SEQ ID NO:1), wherein $X_{01}$ is Ala Asp; $X_{02}$ is Leu, homoArg or Arg; $X_{03}$ is Arg or Ala; and $X_{04}$ is Phe or Trp. One PTH derivative, PTH (1-20) that the invention provides has the amino acid sequence AlaValAlaGluIleGlnLeuMetHis$X_{01}$ $X_{02}X_{03}$Lys$X_{04}$LeuAsnSerMet$X_{05}$Arg (SEQ ID NO:25), wherein $X_{05}$ is Arg or Ala. Another PTH derivative, PTH (1-22) that the invention provides has the amino acid sequence AlaValAlaGluIleGlnLeuMetHis$X_{01}X_{02}X_{03}$ Lys$X_{04}$LeuAsnSerMet$X_{05}$ArgValGlu (SEQ ID NO:26), wherein $X_{05}$ is Arg or Ala. Another PTH derivative, PTH (1-24) that the invention provides has the amino acid sequence AlaValAlaGluIleGlnLeuMetHis$X_{01}X_{02}X_{03}$Lys $X_{04}$LeuAsnSerMet$X_{05}$ArgValGluTrpLeu (SEQ ID NO:27), wherein $X_{05}$ is Arg or Ala. Yet another PTH derivative, PTH (1-26) that the invention provides has the amino acid sequence AlaValAlaGluIleGlnLeuMetHis$X_{01}X_{02}$ $X_{03}$Lys$X_{04}$LeuAsnSerMet$X_{05}$ArgValGluTrpLeuArgLys (SEQ ID NO:28), wherein $X_{05}$ is Arg or Ala. Still another PTH derivative, PTH (1-28) that the invention provides has the amino acid sequence AlaValAlaGluIleGlnLeuMetHis $X_{01}X_{02}X_{03}$Lys$X_{04}$LeuAsnSerMet$X_{05}$ArgValGluTrp LeuArgLysLysLeu (SEQ ID NO:29), wherein $X_{05}$ is Arg or Ala. Another PTH derivative, PTH (1-30) that the invention provides has the amino acid sequence AlaValAla GluIleGlnLeuMetHis$X_{01}X_{02}X_{03}$Lys$X_{04}$LeuAsnSerMet$X_{05}$ ArgValGluTrpLeuArgLysLysLeuGlnAsp (SEQ ID NO:30), wherein $X_{05}$ is Arg or Ala. And another PTH derivative, PTH (1-32) that the invention provides has the amino acid sequence AlaValAlaGluIleGlnLeuMetHis$X_{01}X_{02}X_{03}$ Lys$X_{04}$LeuAsnSerMet$X_{05}$ArgValGluTrpLeuArgLysLysLeu GlnAspValHis (SEQ ID NO:31), wherein $X_{05}$ is Arg or Ala. Alternatively, an embodiment of the invention may substitute Serine for Ala-3. In yet another embodiment, at least one of $X_{01}X_{02}X_{03}X_{04}$ or $X_{05}$ may be the native amino acid for that position, provided that not all X's are substituted so as to result in the native amino acid sequence for any of the various derivatives of rPTH or HPTH.

The full 34 amino acid sequence of this derivative is AlaValAlaGluIleGlnLeuMetHis$X_{01}X_{02}X_{03}$Lys$X_{04}$LeuAsnSerMetGluArgValGluTrpLeuArgLysLysLeuGlnAspValHisAsp$X_{05}$ (SEQ ID NO:16) or SerValAlaGluIleGlnLeuMetHis$X_{01}X_{02}X_{03}$Lys$X_{04}$LeuAlaSerValGluMetGlnGluTrpLeuArgLysLysLeuGlnAspValHisAsp$X_{05}$ (SEQ ID NO:21) wherein $X_{01}$ is Ala Asp; $X_{02}$ is Leu, homoArg or Arg; $X_{03}$ is Arg or Ala; $X_{04}$ is Phe or Trp and $X_{05}$ is Phe or Tyr. Alternatively, an embodiment of the invention may substitute Serine for Ala-3, in any of the PTH derivatives. In yet another embodiment, at least one of $X_{01}$, $X_{02}$, $X_{03}$, $X_{04}$ or $X_{05}$ may be the native amino acid for that position, provided that not all X's are substituted so as to result in the native PTH(1-34) of either rat or human. A specific embodiment of the invention is drawn to a polypeptide having the sequence AlaValAlaGluIleGlnLeuMetHisAlaArgAlaLysHisLeuAsnSerMetGluArgValGluTrpLeuArgLysLysLeuGlnAspValHisAspTyr (SEQ ID NO:12). AlaValAlaGluIleGlnLeuMetHisAlaArgAlaLysHisLeuAlaSerValGluArgMetGlnTrpLeuArgLysLysLeuGlnAspVaLHisAspTyr-(SEQ ID No:20), AlaValAlaGluIleGlnLeuMetHisAlaArgAlaLysHisLeuAsnSerMetGluArgValGluTrpLeuArgLysLysLeuGlnAspValHisAspTyr (SEQ ID No:22), AlaValAlaGluIleGlnLeuMetHisAlaArgAlaLysHisLeuAlaSerValArgArgMetGlnTrpLeuArgLysLysLeuGlnAspValHisAspTyr (SEQ ID No:23) and AlaValAlaGluIleGlnLeuMetHisAlaArgAlaLysHisLeuAsnSerMetArgArgValGluTrpLeuArgLysLysLeuGlnAspValHisAspTyr (SEQ ID No:24). In yet another embodiment of the invention, any of the PTH(1-34) polypeptides of the invention may substitute Glu-19 with an Arg.

The invention is further drawn to fragments of the PTH derivatives of the invention or polypeptides similar to the PTH derivatives such that conservative amino acid substitutions are made in the polypeptide sequences.

The invention further provides both synthetic and recombinant biologically active polypeptide derivatives of PTH (1-14), PTH(11-20), PTH(11-22), PTH(1-24), PTH(1-26), PTH(1-28), PTH(1-30), PTH(1-32) and PTH(1-34) Preferable embodiments of the invention contain amino acids 1-9,1-10, 1-11, 1-12, and 1-13. The invention also is directed to pharmaceutical salts and N-or C-terminal derivatives of the polypeptides described above.

A preferable embodiment of the invention is drawn to any of the above recited polypeptides, wherein said polypeptide contains a C-terminal amide. Examples of PTH polypeptide derivatives with a C-terminal amide include, but are not limited to: AlaValAlaGluIleGlnLeuMetHisAlaArgAlaLysHis-amide (SEQ IDNo:3), AlaValSerGluIleGlnLeuMetHisAsnArgGlyLysHis-amide(SEQ ID No:4), AlaValSerGluIleGlnLeuMetHisAsnArgAlaLysHis-amide (SEQ ID No:5), AlaValAlaGluIleGlnLeuMetHisAsnArgAlaGluHis-amide (SEQ ID No:6), AlaValAlaGluIleGlnLeuMetHisAlaArgAlaLysTrp-amide (SEQ ID No:7), and AlaValAlaGluIleGlnLeuMetHisGlnArgAlaLysHis-amide (SEQ ID No:8), AlaValAlaGluIleGlnLeuMetHisAlaArgAlaLys-amide (SEQ ID No:9), AlaValAlaGluIleGlnLeuMetHisAlaArgAla-amide (SEQ ID No:10), AlaValAlaGluIleGlnLeuMetHisAlaArg-amide (SEQ ID No:11), AlaValAlaGluIleGlnLeuMetHisAlaArgAlaLysHisLeuAsnSerMetGluArgValGluTrpLeuArgLysLysLeuGlnAspValHisAspTyr-amide (SEQ ID No:12), AlaValSerGluIleGlnLeuMetHisAlaArgAlaLysHis-amide (SEQ ID No:13), AlaValAlaGluIleGlnLeuMetHisAlaArgAlaLysFisLeuAlaSerValGluArgMetGlnTrpLeuArgLysLysLeuGlnAspValHisAspTyr-amide (SEQ ID No:20), AlaValAlaGluIleGlnLeuMetHisAlaArgAlaLysHisLeuAsnSerMetGluArgvalGluTrpLeuArgLysLysLeuGlnAspValHisAspTyr-amide (SEQ ID No:22) AlaValAlaGluIleGlnLeuMetHisAlaArgAlaLysHisLeuAlaSerValArgArgMetGlnTrpLeuArgLysLysLeuGlnAspValHisAspTyr-amide (SEQ ID No:23) and AlaValAlaGluIleGlnLeuMetHisAlaArgAlaLysHisLeuAsnSerMetArgArgValGluTrpLeuArgLysLysLeuGlnAspValHisAspTyr-amide (SEQ ID No:24).

Embodiments of the invention are also drawn to polypeptides having amino acids comprising any of the sequences described herein or to a polypeptide comprising any of the sequences described herein. Similarly the invention is also drawn to polynucleotides having nucleic acids comprising any of the sequences described herein or to a polynucleotide comprising any of the sequences described herein.

The invention is further drawn to a PTH 1-14 polypeptide that has a single amino acid substitution relative to the native rat or human PTH (SEQ: ID No 14 and SEQ ID NO:17): In some embodiments the single amino acid substitution increases cAMP stimulation relative to the native PTH in HKRK-B7 cells, while in other embodiments the substitution decreases the ability of PTH to stimulate cAMP in HKRK-B7 cells.

A preferable embodiment of the invention that increases cAMP stimulation has a single amino acid substitution in PTH 1-14 that is selected from the group consisting of one of the following substitutions.

(a) Asn-10-->Asp, Glu or Gln;
(b) Leu-11-->Ile, Met, Lys, Arg or Trp;
(c) Gly-12-->Arg or His;
(d) Lys-13-->Leu, Arg, His or Trp; and
(e) His-14-->Leu, Arg, Phe or Trp.

The above language means that, for example, the amino acid asparagine at position 10 in the native polypeptide may be substituted with any one of Asp, Glu or Gln. Similarly, Lys-13 may be replaced with Leu, Arg, His or Trp. Preferable embodiments of the claimed invention are polypeptides that contain amino acids 1-9,1-10, 1-11, 1-12, 1-13, 1-14 or 1-34 of PTH.

The invention is further drawn to derivatives of fragments of PTH(1-34) polypeptides that have a single amino acid substitution relative to the native rat or human PTH (SEQ: ID No18 and SEQ ID No:19). In some embodiments the single amino acid substitution increases cAMP stimulation relative to the native PTH in HKRK-B7 cells, while in other embodiments the substitution decreases the ability of PTH to stimulate cAMP in HKRK-B7 cells.

A preferable embodiment of the invention is a polypeptide selected from the group: PTH(1-20), PTH(1-22), PTH(1-24), PTH(1-26), PTH(1-28), PTH(1-30) and PTH(-1-32) which has a single amino acid substitution that increases cAMP stimulation. Preferably, the amino acid substitution responsible for increasing cAMP stimulation HKRK-B7 cells is selected from the group consisting of one of the following substitutions.

(a) Asn-10-->Asp, Glu or Gln;
(b) Leu-11-->Ile, Met, Lys, Arg or Trp;
(c) Gly-12-->Arg or His;
(d) Lys-13-->Leu, Arg, His or Trp;
(e) His-14-->Leu, Arg, Phe or Trp; and
(f) Glu19-->Arg.

The above language means that, for example, the amino acid asparagine at position 10 in the native polypeptide may be substituted with any one of Asp, Glu or Gln. Similarly, Lys-13 may be replaced with Leu, Arg, His or Trp. Preferable embodiments of the claimed invention are polypeptides that contain amino acids 1-9, 1-10, 1-11, 1-12, 1-13, 1-14, 1-20, 1-22, 1-24, 1-26, 1-28, 1-30 or 1-32 of PTH.

The invention is further drawn to a PTH (1-14) polypeptide wherein a single amino acid substitution reduces cAMP stimulation relative to the native PTH in HKRK-B7 cells, provided that said substitution is not alanine at any position, the substitution at Ser-1 is not Tyr, Pro or Asp, the substitution at Val-2 is not Leu, Ser, Arg or Glu, the substitution at Ser-3 is not Thr, Gly, Ile, or Asn and the substitution at Glu-4 is not Gly, His, Lys, Val or Asp.

The invention is further drawn to any of the above polypeptides labeled with a label selected from the group consisting of: a radiolabel, a flourescent label, a bioluminescent label, or a chemiluminescent label. In a preferable embodiment the radiolabel is $^{99m}$Tc.

In accordance with yet a further aspect of the invention, this invention also provides pharmaceutical compositions comprising a PTH derivative and a pharmaceutically acceptable excipient and/or a pharmaceutically acceptable solution such as saline or a physiologically buffered solution.

The invention further provides a recombinant or isolated DNA molecule encoding any of the polypeptide derivatives of the invention. A preferable embodiment of the invention provides a recombinant or isolated DNA molecule comprising: (1) an expression control region, said region operably linked with (2) a polynucleotide sequence coding a PTH derivative. Preferable embodiments of the invention include a polynucleotide encoding a PTH derivative selected from the group consisting of: AlaValAlaGluIleGlnLeuMetHis$X_{01}X_{02}X_{03}$Lys$X_{04}$ (SEQ ID NO:1) wherein: $X_{01}$ is Ala, Asp or Gln; $X_{02}$ is Leu or Arg; $X_{03}$ is Arg or Ala; and $X_{04}$ is Phe or Trp; AlaValAlaGluIleGlnLeuMetHis$X_{01}$ArgAlaLys$X_{02}$(SEQ ID NO:2), wherein: $X_{01}$ is Ala, Asp or Gln; and $X_{02}$ is Trp or His. AlaValAlaGluIleGlnLeuMetHisAlaArgAlaLysHis (SEQ ID No:3), AlaValSerGluIleGlnLeuMetHisAsnArgGlyLysHis (SEQ ID No:4), AlaValSerGluIleGlnLeuMetHisAsnArgAlaLysHis (SEQ ID No:5), AlaValAlaGluIleGlnLeuMetHisAsnArgAlaLysHis (SEQ ID No:6), AlaValAlaGluIleGlnLeuMetHisAlaArgAlaLysTrp (SEQ ID No:7), and AlaValAlaGluIleGlnLeuMetHisGlnArgAlaLysHis (SEQ ID No:8). AlaValAlaGluIleGlnLeuMetHisAlaArgAlaLys (SEQ ID No: 9), AlaValAlaGluIleGlnLeuMetHisAlaArgAla (SEQ ID NO:10), AlaValAlaGluIleGlnLeuMetHisAlaArg (SEQ ID No:11), AlaValAlaGluIleGlnLeuMetHisAlaArgAlaLysHisLeuAsnSerMetGluArgValGluTrpLeuArgLysLysLeuGlnAspValHisAspTyr (or Phe) (SEQ ID NO:12) and AlaValSerGluIleGlnLeuMetHisAlaArgAlaLysHis (SEQ ID No:13). Preferable embodiments also include control regions that are bacterial, viral, fungal or mammalian promoters.

The invention further relates to methods of making the polypeptides of the invention. Preferable embodiment include making the polypeptides using liquid or solid phase synthesis or recombinant DNA techniques.

A preferable embodiment of the invention relates to methods of making recombinant vectors comprising the DNA encoding polypeptides of the invention. Preferable embodiments further include making and preparing the polypeptides by introducing recombinant DNA molecules of the invention into a host cell and expressing the polypeptide encoded by said molecules. The host may be either prokaryotic or eukaryotic. Preferable embodiments include a host cell that is bacterial or mammalian.

In accordance with yet a further aspect of the invention, this invention provides a method for treating mammalian conditions characterized by decreases in bone mass, which method comprises administering to a subject in need thereof an effective bone mass-increasing amount of a biologically active PTH polypeptide. A preferable embodiment of the invention is drawn to conditions such as osteoporosis. The types of osteoporosis include, but are not limited to old age osteoporosis and postmenopausal osteoporosis. Additional preferable embodiments include using an effective amounts of the polypeptide of about 0.01 µg/kg/day to about 1.0 µg/kg/day wherein the polypeptide may be administer parenterally, subcutaneously or by nasal insufflation.

The invention further relates to a method for treating decreases in bone mass wherein said effective bone mass-increasing amount of said polypeptide is administered by providing to the patient DNA encoding said polypeptide and expressing said polypeptide in vivo.

In accordance with yet a further aspect of the invention, this invention also provides a method for determining rates of bone reformation, bone resorption and/or bone remodeling comprising administering to a patient an effective amount of a labeled PTH polypeptide, such as for example, SEQ ID NO:1 or a derivatives thereof and determining the uptake of said peptide into the bone of said patient. The peptide may be labeled with a label selected from the group consisting of: radiolabel, flourescent label, bioluminescent label, or chemiluminescent label. An example of a suitable radiolabel is $^{99m}$Tc.

A further aspect of the invention is drawn to amino-acid substitutions at positions 1-14 in the polypeptide that produce a PTH derivative to antagonize or agonize the PTH-1/PTH-2 receptor.

The invention is further related to a method of increasing cAMP in a mammalian cell having PTH-1 receptors, said method comprising contacting the cell with a sufficient amount of the polypeptide of the invention to increase cAMP.

The invention is further related to a method of increasing inositol phosphate in a mammalian cell having PTH-1 receptors, said method comprising contacting the cell with a sufficient amount of the polypeptide of the invention to increase inositol phosphate.

For the sequences of polypeptides referred to in FIGS. 2-7, see for example—Table 2, 3 or 4.

Figure 1A:
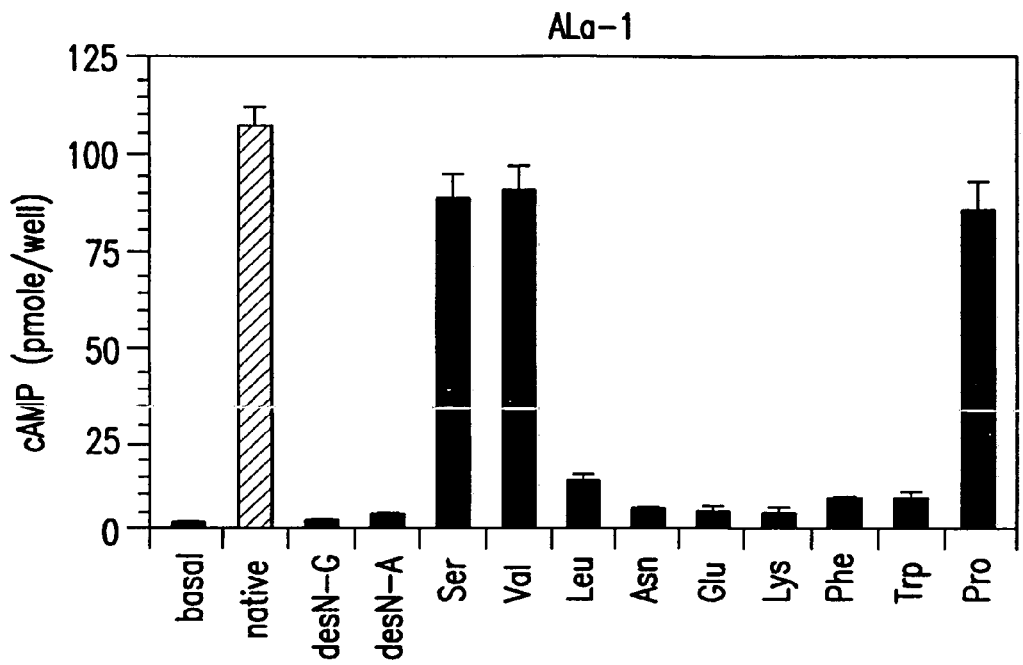
FIGS. 1A-1N. Effects of single mutations in PTH(1-14). Each graph shows the effects on cAMP signaling in HKRK-B7 cells of single amino acid substitutions at the position in native rPTH(1-14) indicated above the graph. HKRK-B7 cells are a clonal derivative of the porcine kidney cell line, LLC-PK1, that is stably transfected with the human PTH-1 receptor. Each peptide was tested at a dose of 100 µM. All peptides shown were tested in duplicate and concurrently; and the experiment was repeated twice. The data are combined averages (±) S.E.M. from the two experiments.
Figure 1B:
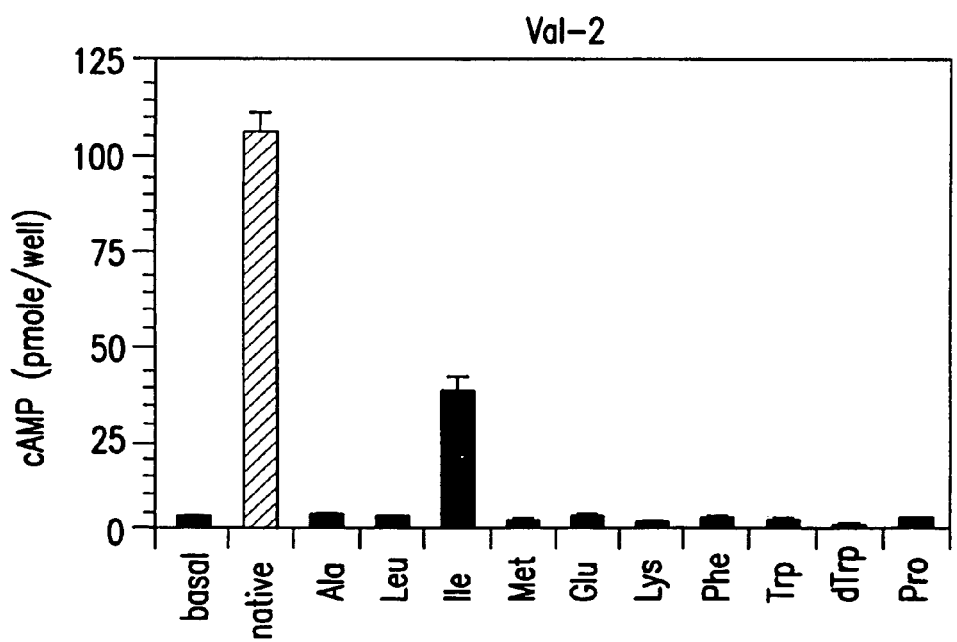
Figure 1C:
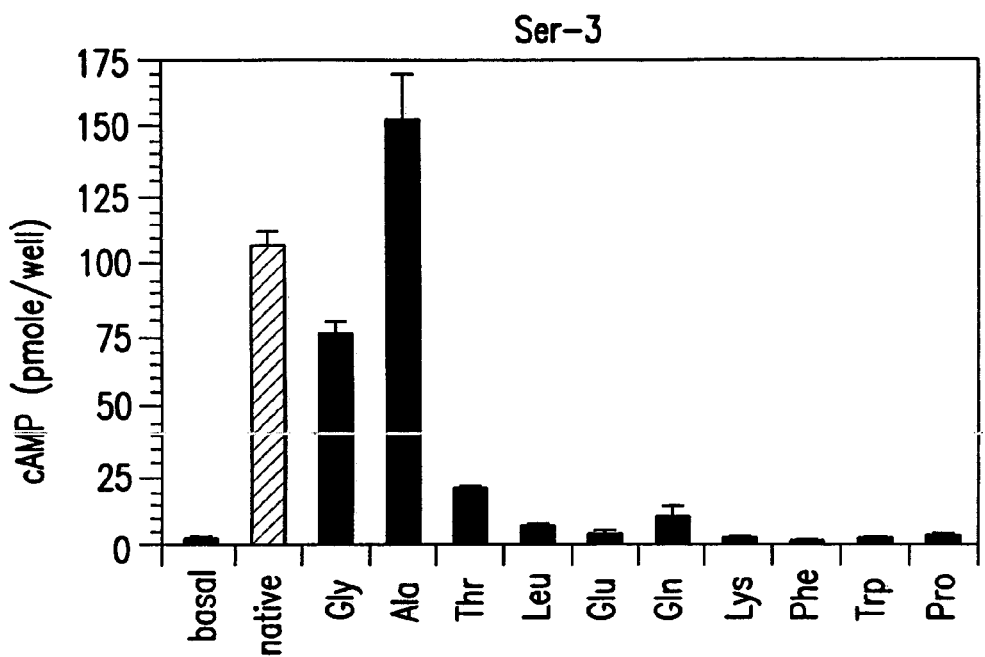
Figure 1D:
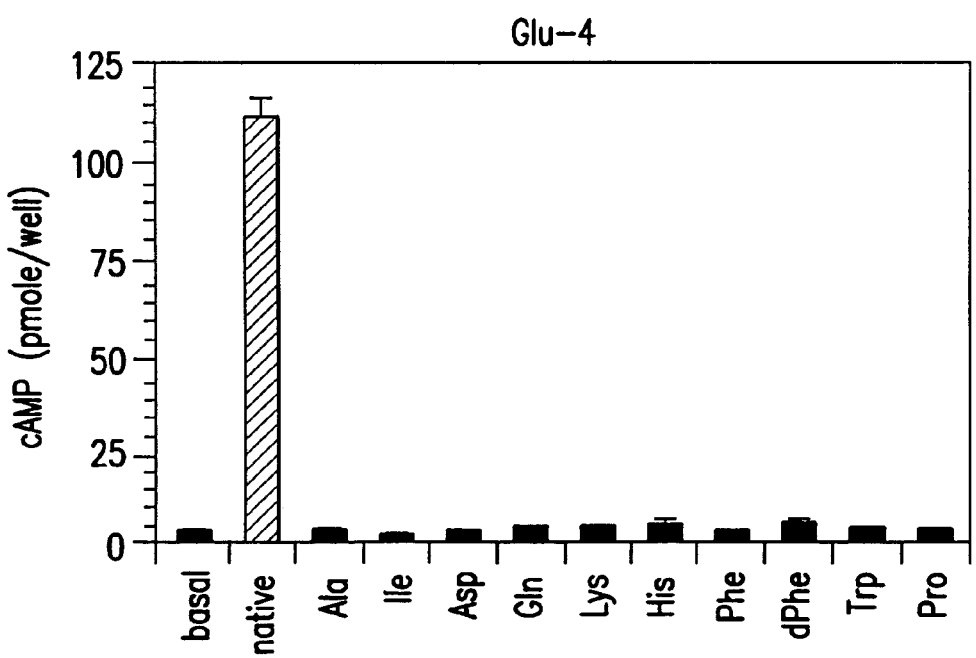
Figure 1E:
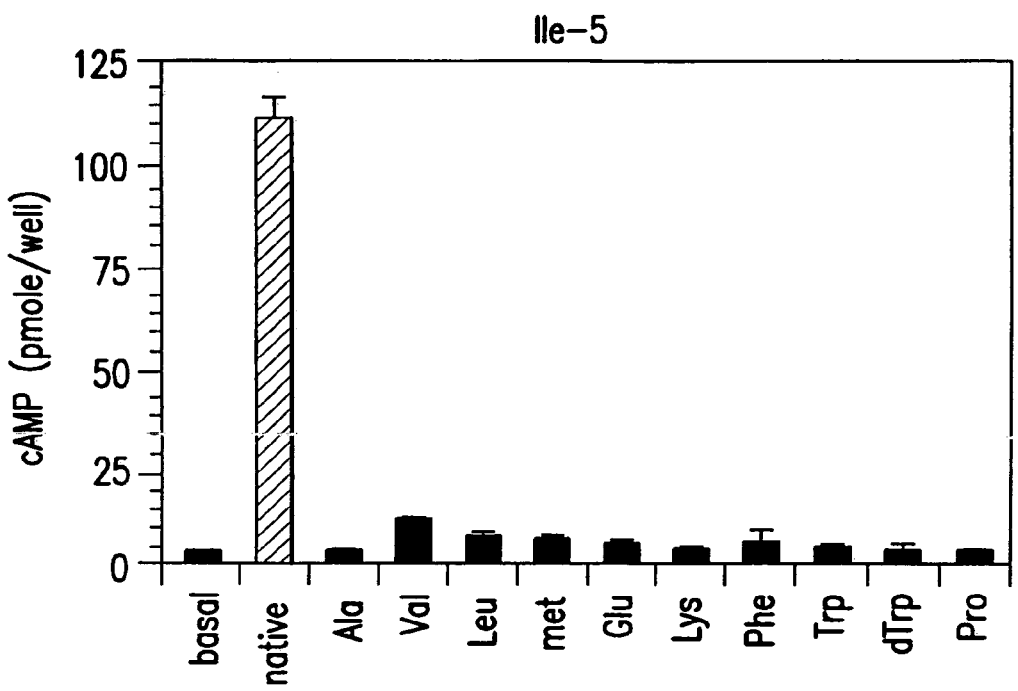
Figure 1F:
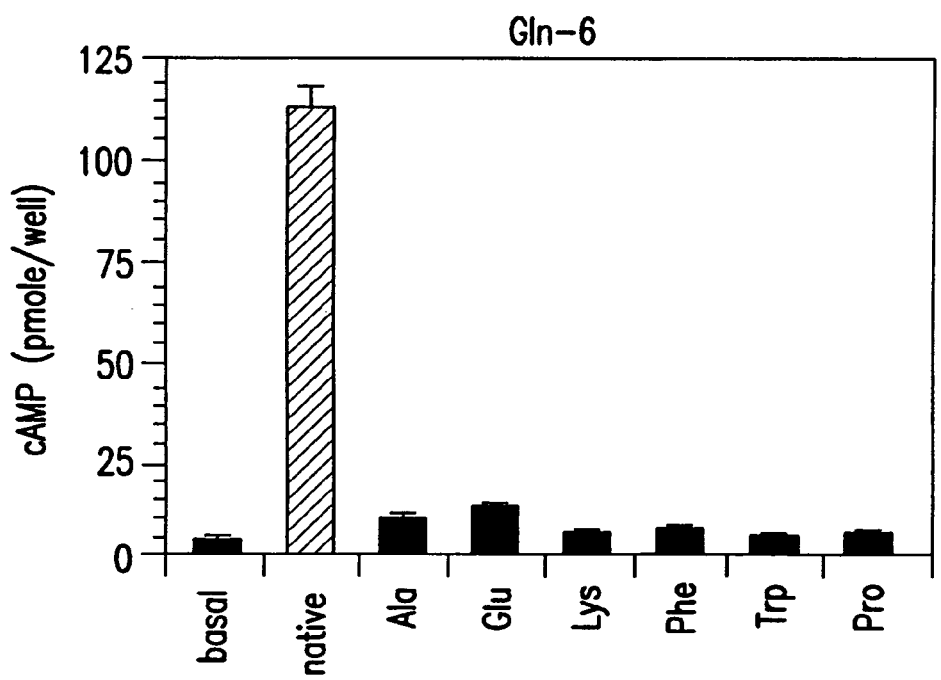
Figure 1G:
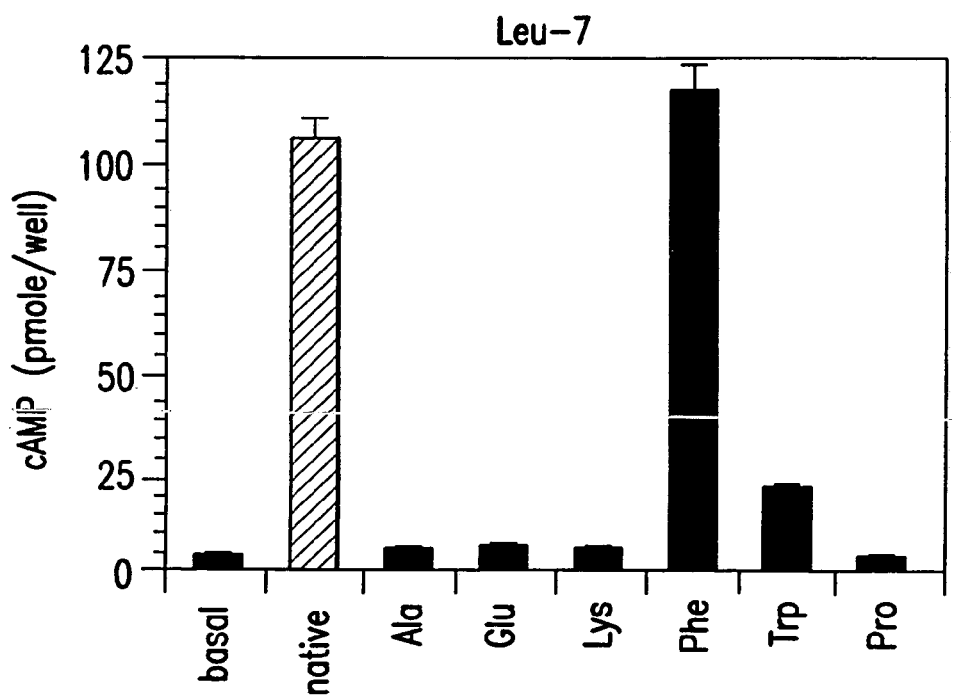
Figure 1H:
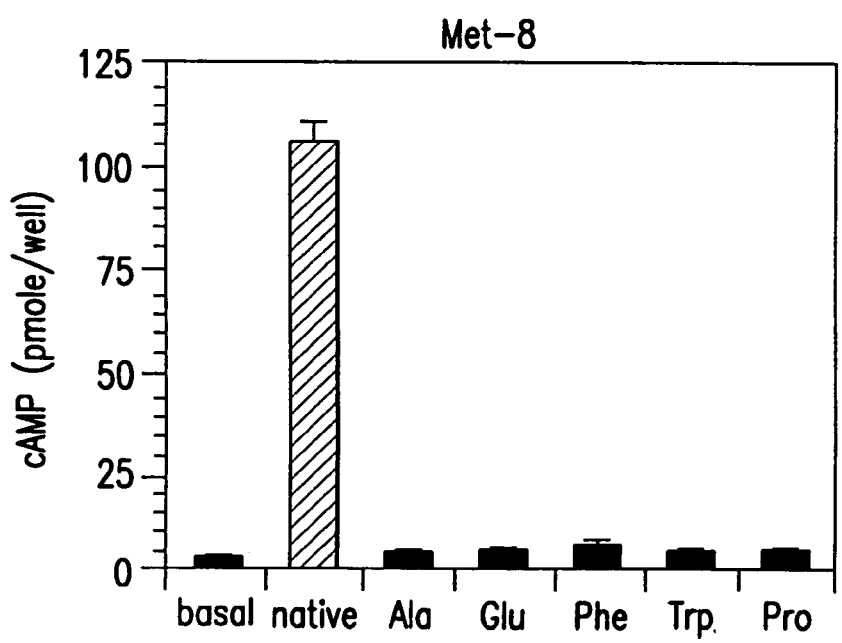
Figure 1I:
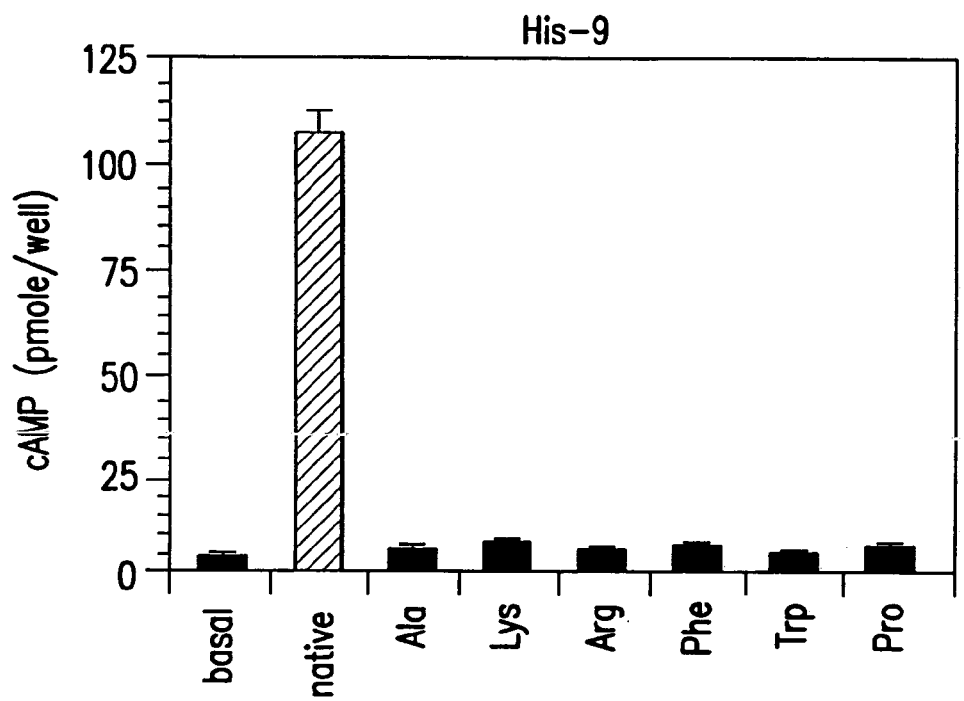
Figure 1J:
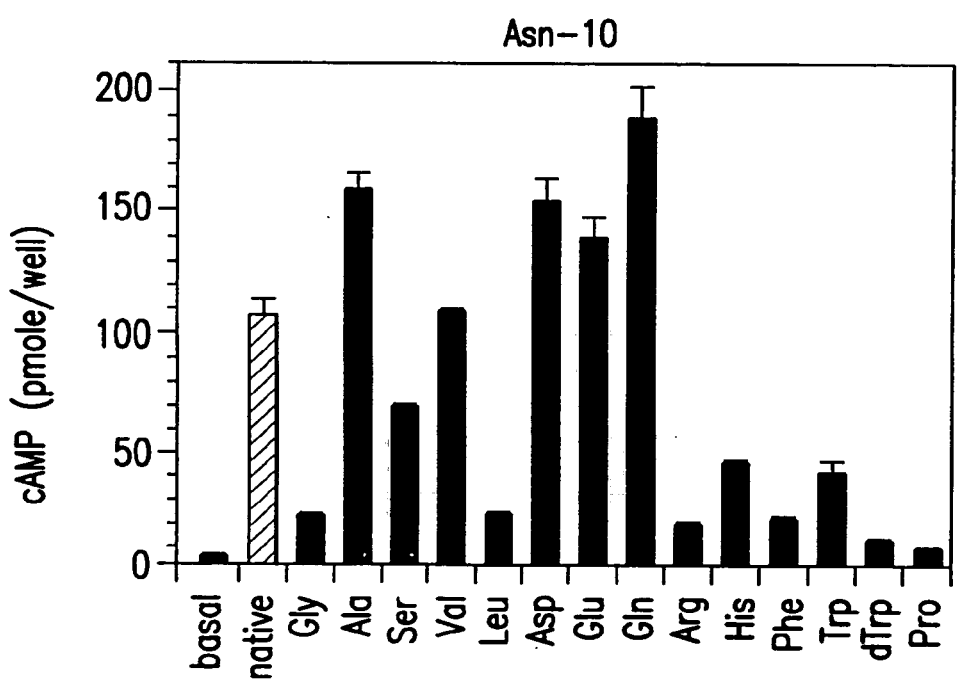
Figure 1K:
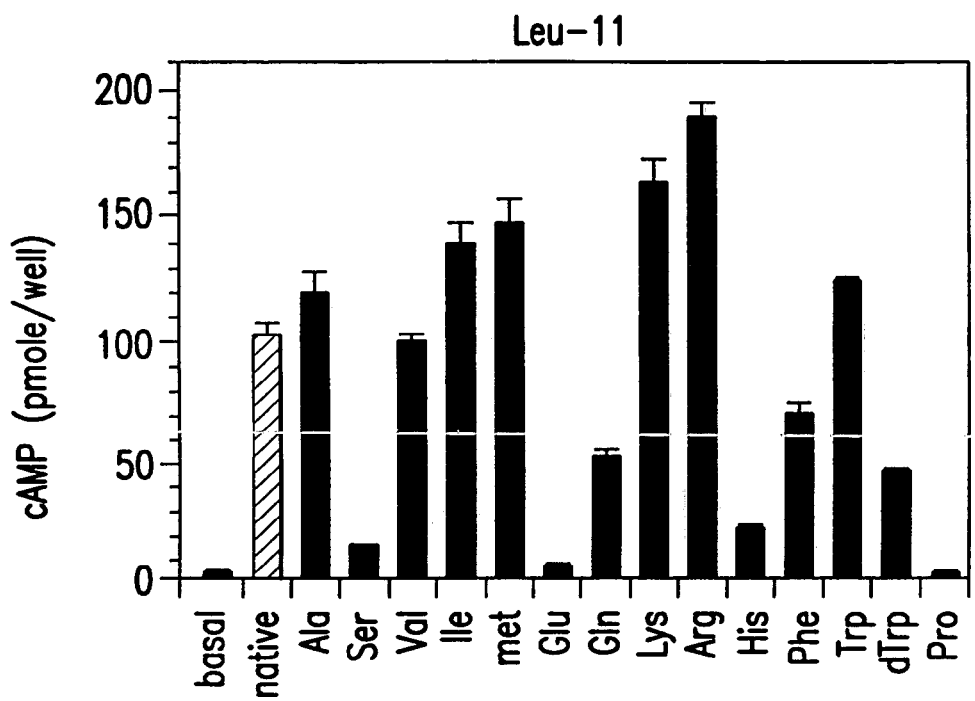
Figure 1L:
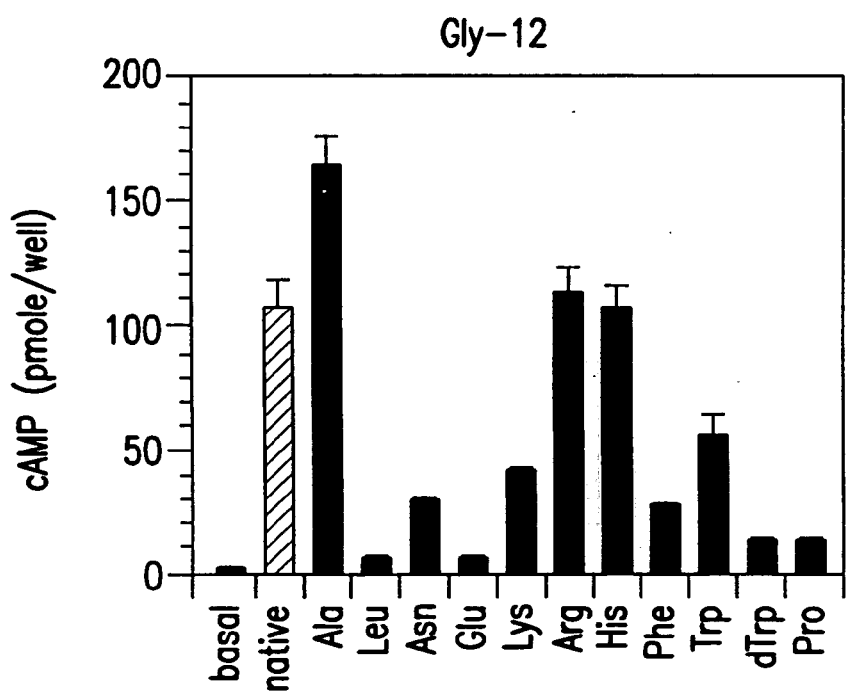
Figure 1M:
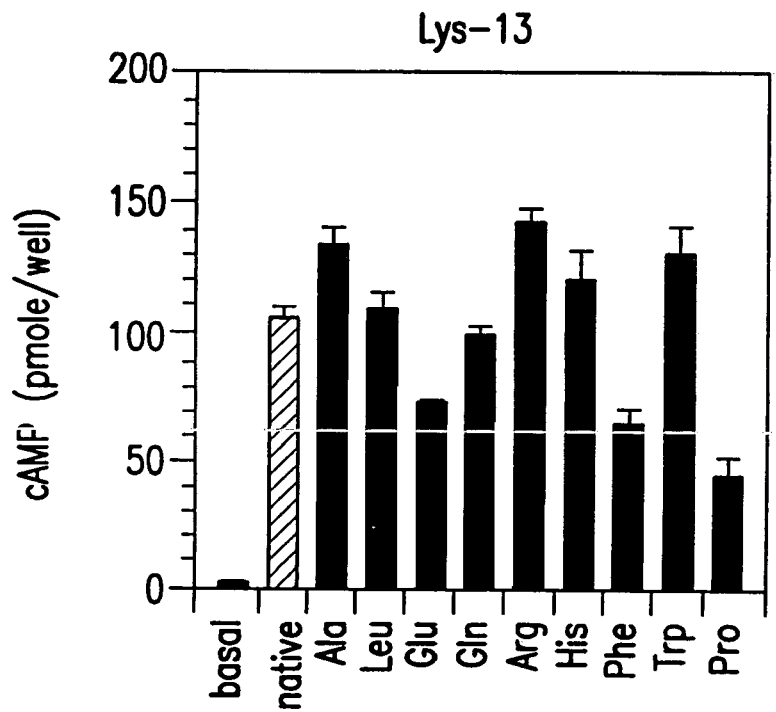
Figure 1N:
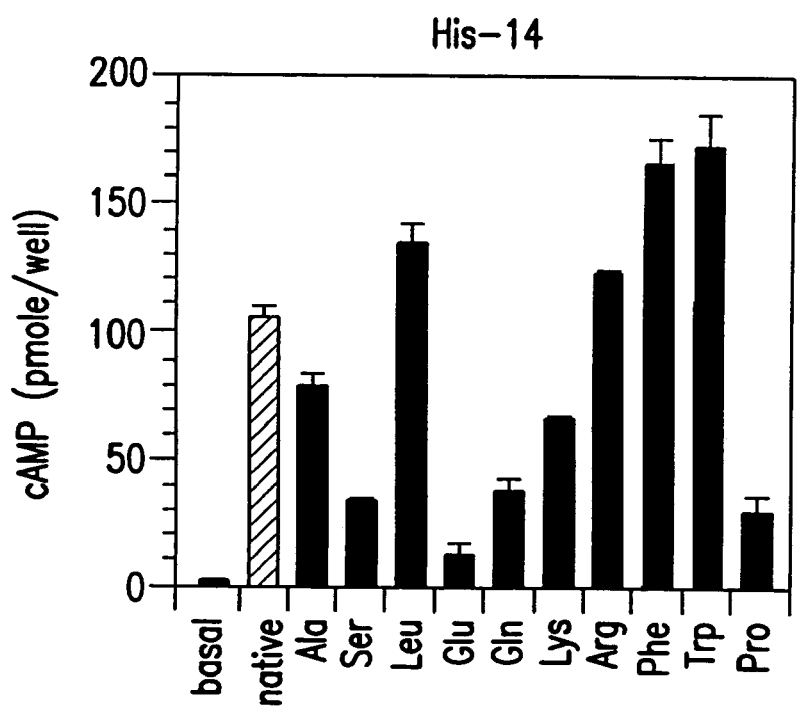
Figure 2A:
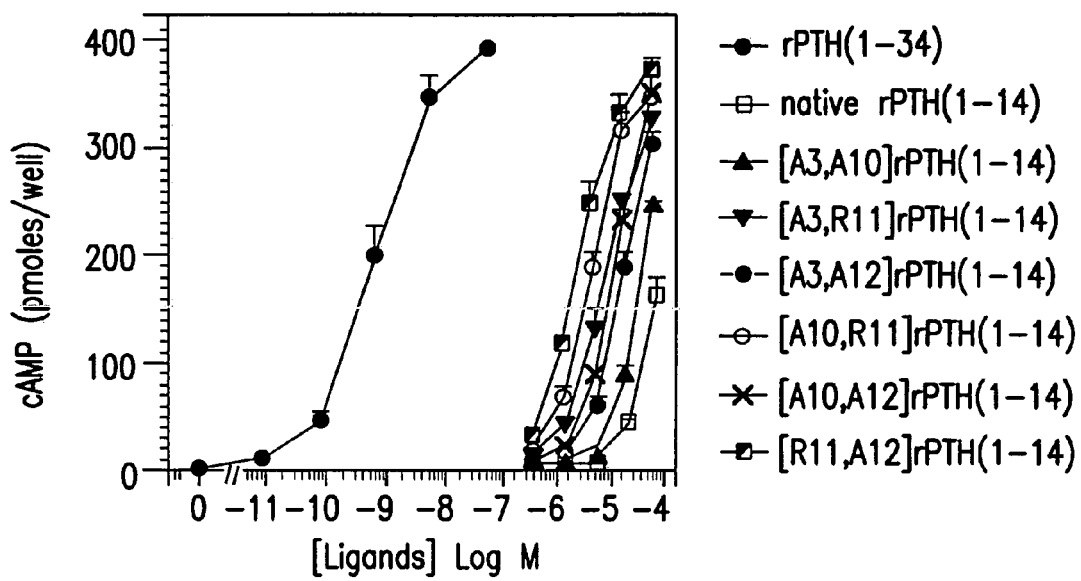
Figure 2B:
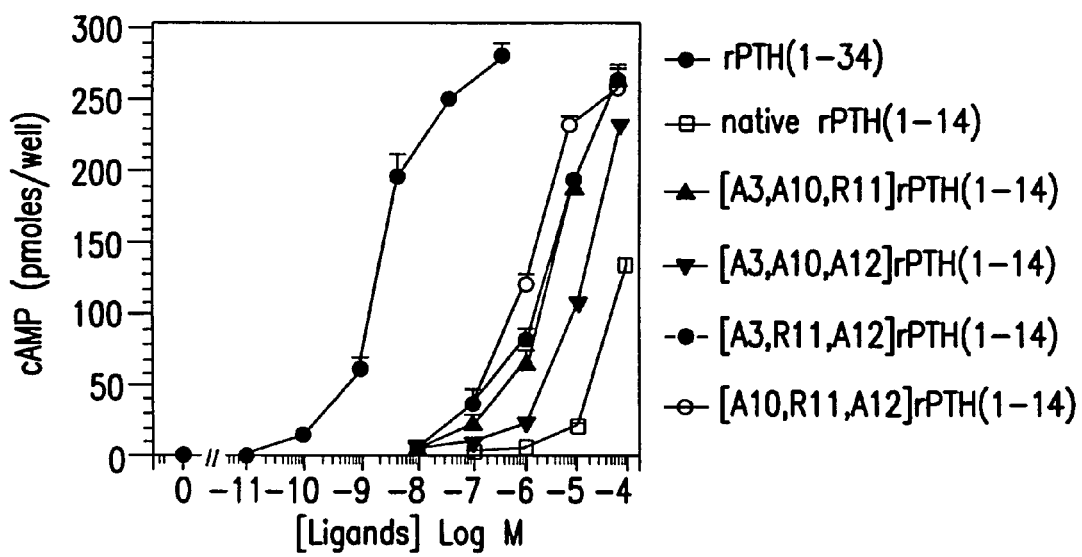
Figure 2C:
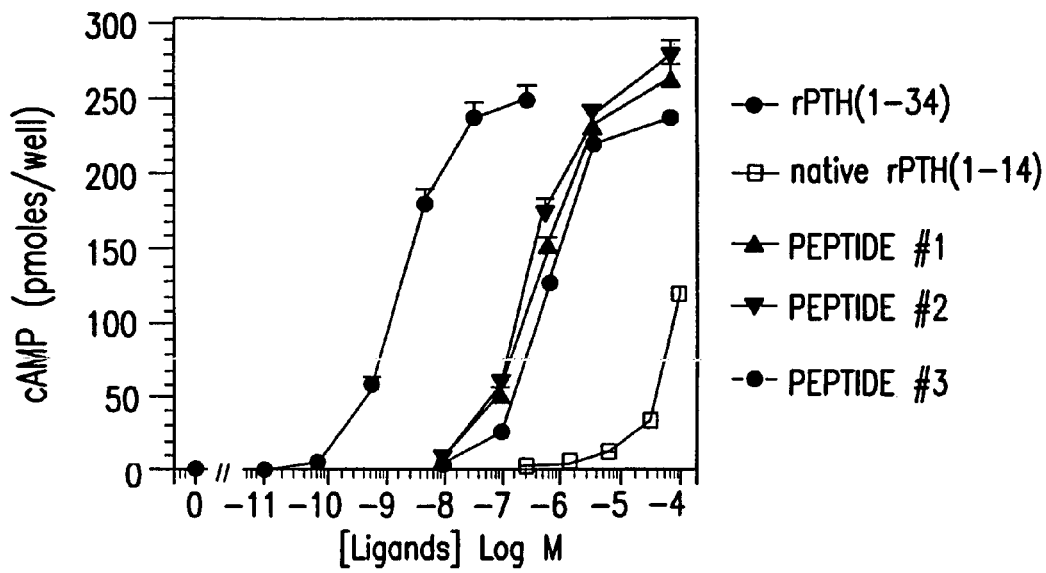

FIG. 2A-2C. Dose-Response analysis of substituted PTH (1-14) analogs. PTH(1-14) analogs with either double (FIG. 2A), triple (FIG. 2B) or four and five substitutions (FIG. 2C) were tested at varying doses for cAMP stimulating activity in HKRK-B7 cells. As controls, native rPTH(1-14), rPTH (1-34) and [Nleu$^{8,21}$Tyr$^{34}$rPTH(1-34)amide were also tested. The symbols correspond to the peptides indicated in the legend. Each graph show data combined from three separate experiments (mean±S.E.M.), each performed in duplicate.

Figure 3:
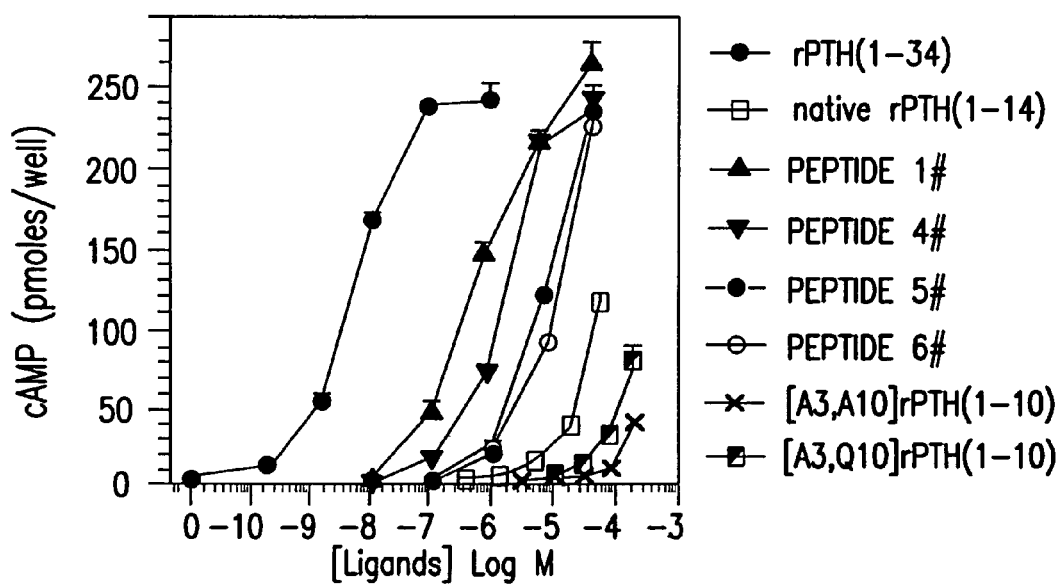

FIG. 3. Dose-Response analysis of substituted PTH analogs in HKRK-B7 cells. The PTH analogs indicated in the legend were tested at varying doses for cAMP stimulating activity in HKRK-B7 cells. Each curve shows data combined from three or more separate experiments (mean±S.E.M.), each performed in duplicate.

Figure 4:
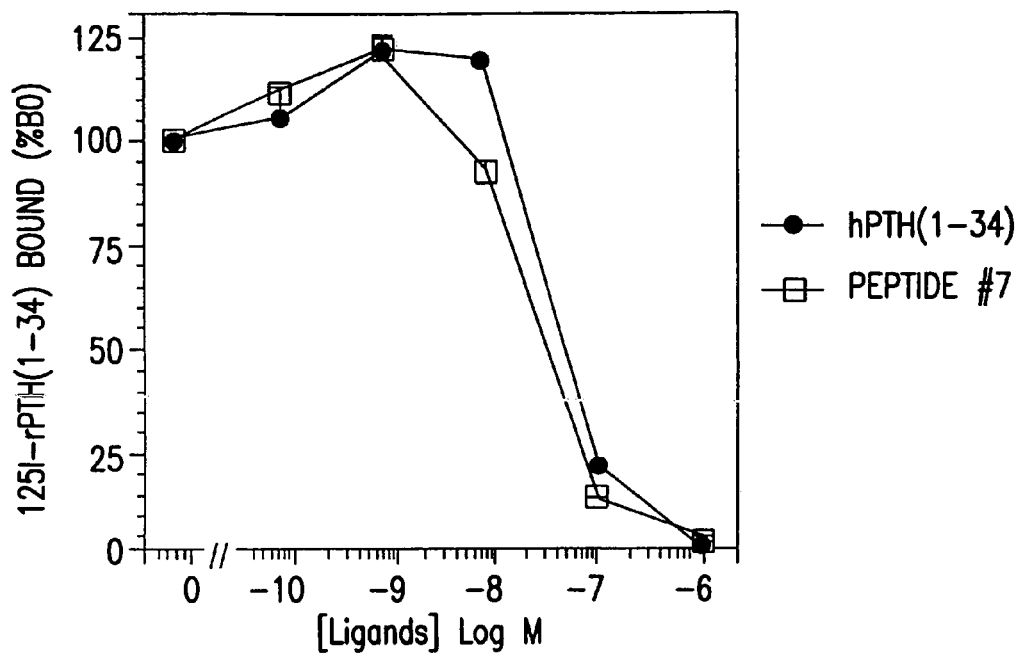

FIG. 4. Binding of PTH analogs in HK-B7. The parent control peptide, hPTH(1-34), and the PTH(1-34) analog (peptide#7), were tested at varying doses for the ability to inhibit the binding of $^{125}$I-rPTH(1-34) (100,000 CPM/well) to HKRK-B7 cells. The data are the mean±S.E.M. of duplicate values from a single experiment.

Figure 5:
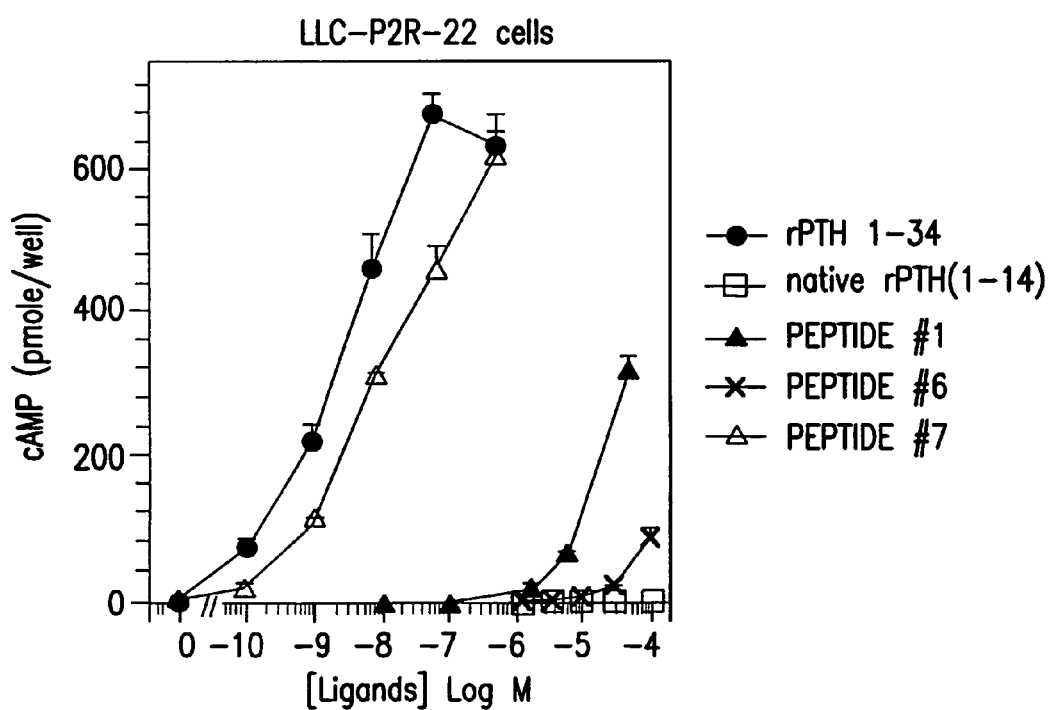

FIG. 5. Dose-Response analysis of substituted PTH analogs in PTH-2 receptor expressing cells. The PTH analogs indicated in the legend were tested at varying doses for the ability to stimulate cAMP formation in LLC-PK1 cells stably transfected with the PTH-2 receptor. The data are the mean±S.E.M. of duplicate values from a single experiment.

Figure 6A:
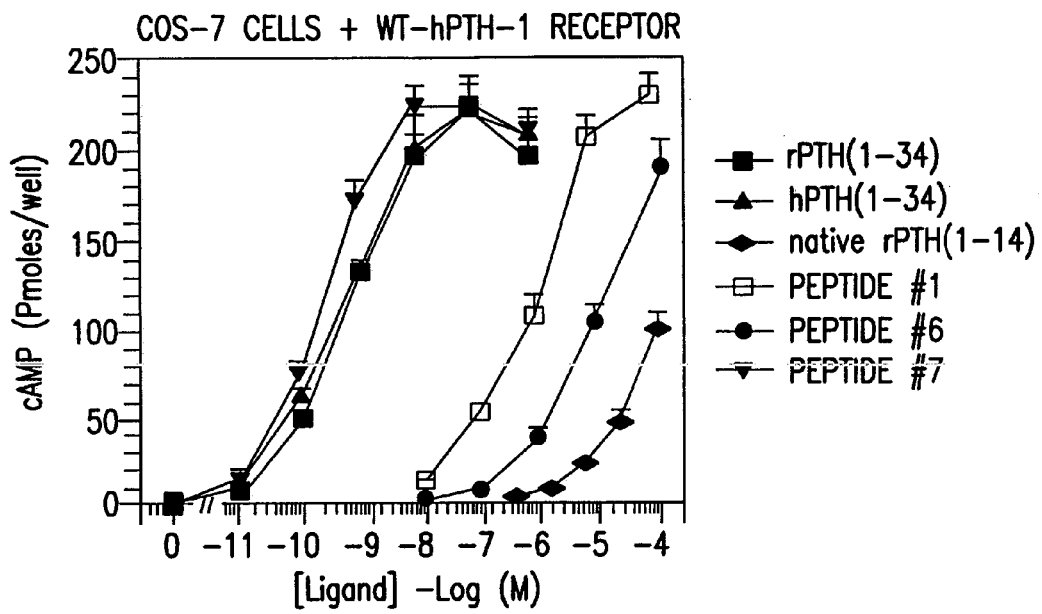
Figure 6B:
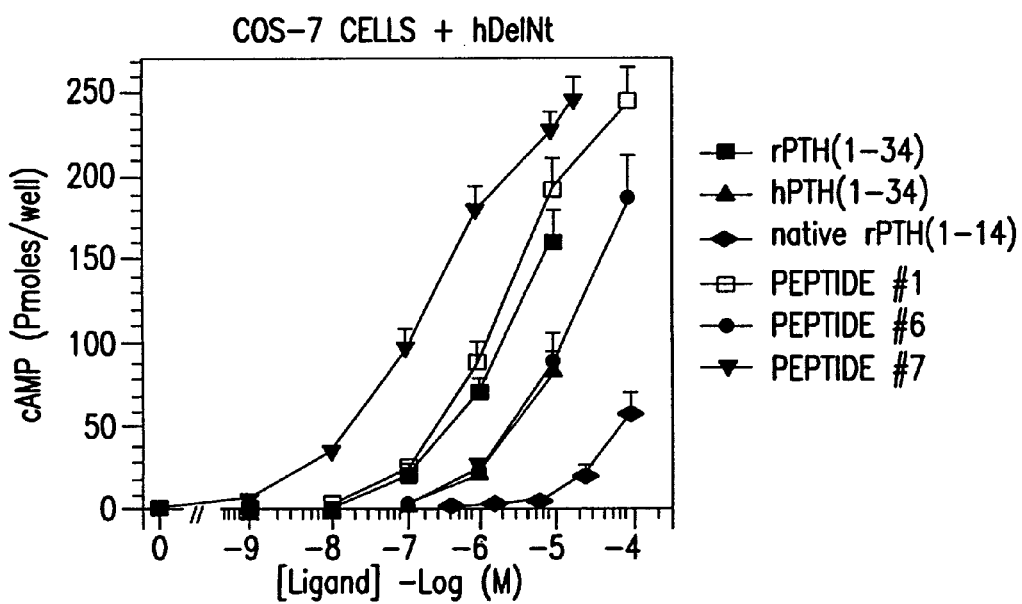

FIG. 6A-6B. Dose-Response analysis of substituted PTH analogs in COS-7 cells. COS-7 cells were transiently transfected with intact human PTH-1 receptor (HK-WT) (FIG. 6A) or a truncated PTH-1 receptor lacking most of the amino-terminal domain (hΔNt or hDelNt) (FIG. 6B) and tested for the ability to mediate cAMP production when treated with varying doses of the PTH analogs indicated in the legend. Each graph show data that were combined from three separate experiments (mean±S.E.M.), each performed in duplicate.

Figure 7A:
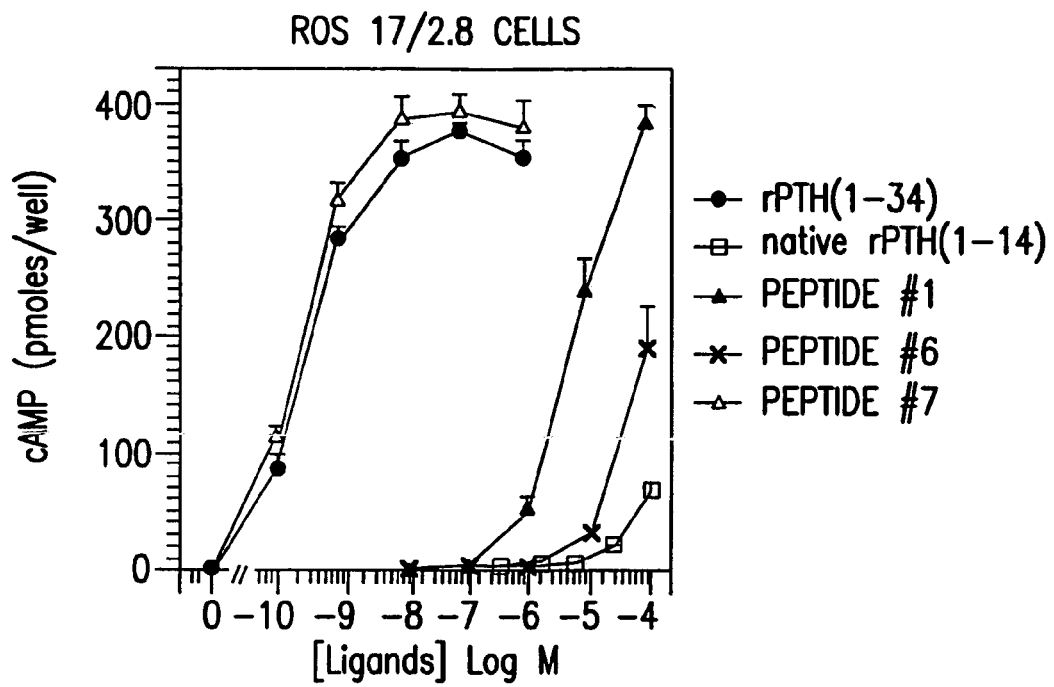
Figure 7B:
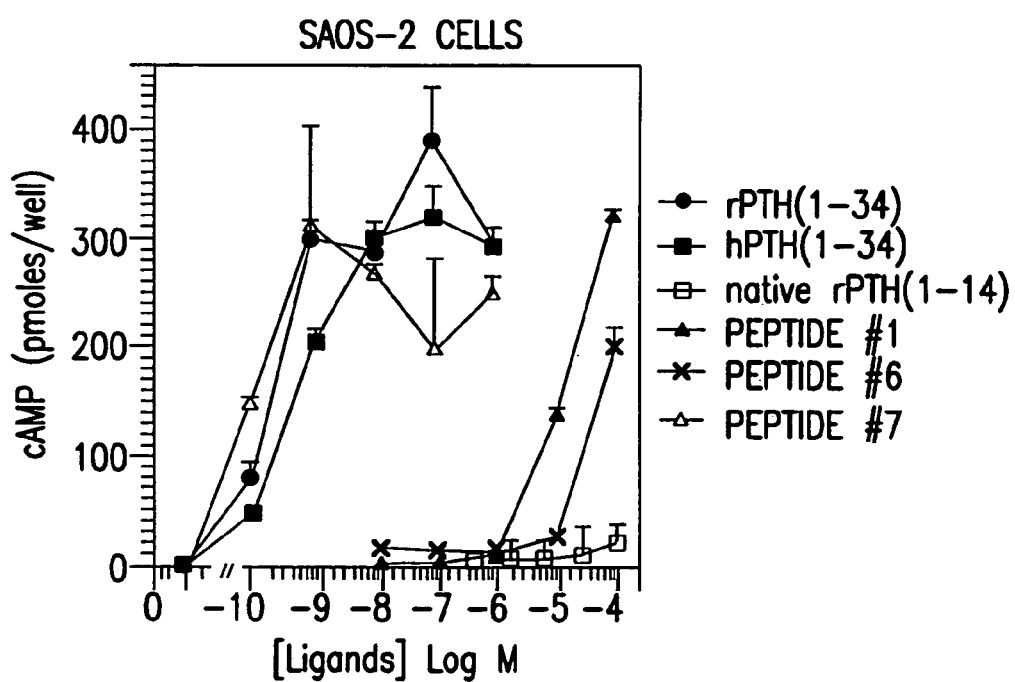

FIG. 7A-7B. Dose-Response analysis of substituted PTH analogs in Osteoblast cells. The osteoblastic cell lines ROS 17/2.8 (FIG. 7A) and SAOS-2 (FIG. 7B), which endogenously express the rat and human PTH-1 receptors, respectively, were treated with the PTH analogs indicated in the legend, and the resulting levels of cAMP were quantified. Each curve in panel A shows the combined cAMP responses (mean±S.E.M.) observed for each peptide in two separate experiments, each performed in duplicate. The curves in panel B are from a single experiment, performed in duplicate.

Figure 8:
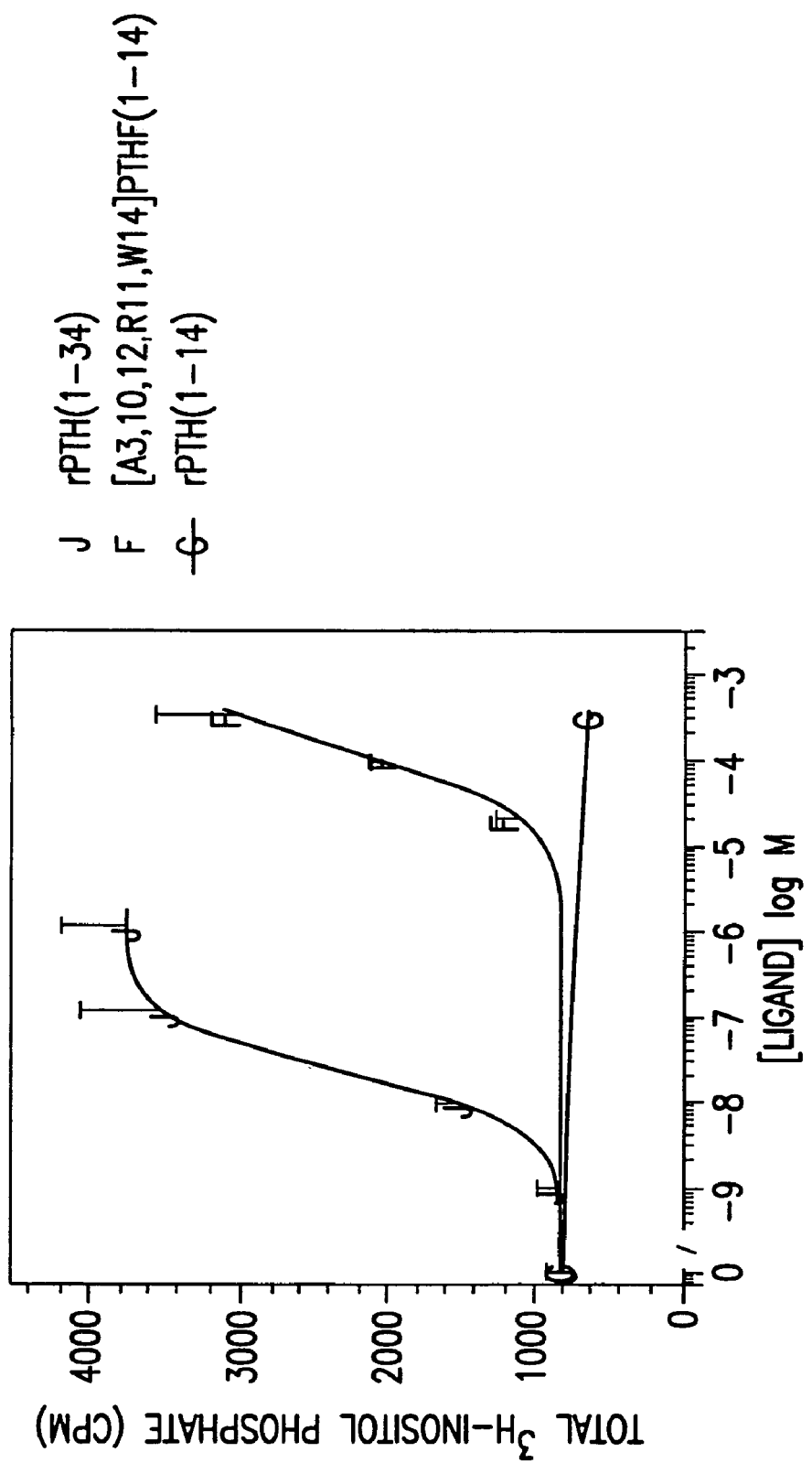

FIG. 8. Dose-Response of PTH (1-14) analogs in COS-7 cells. COS-7 cells were transiently transfected with intact human PTH-1 receptor (HK-WT) and tested for the ability to mediate inositol phosphate production when treated with varying doses of rPTH (1-34) analog, or rPTH (1-14), or a human substituted PTH (1-14) analog, indicated in the legend. Each graph show data that were combined from three separate experiments (mean±S.E.M.), each performed in duplicate.

DETAILED DESCRIPTION OF THE PREFERRED EMBODIMENTS

Definitions

In order to provide a more clear understanding of the specification and claims, the following definitions are provided.

Amino Acid Sequences—The amino acid sequences in this application use either the single letter or three letter designations for the amino acids. These designations are well known to one of skill in the art and can be found in numerous readily available references, such as for example in *Cooper, G. M, The Cell* 1997, ASM Press, Washington, D.C. or Ausubel et al., *Current Protocols in Molecular Biology*, 1994. Where substitutions in a sequence may be referred to, for example, as Ser-3-->Ala, this means that the serine in the third position from the N-terminal end of the polypeptide may be replaced with another amino acid. Alanine in this instance.

Biological Activity of the Protein: This expression refers to any biological activity of the polypeptide. Examples of these activities include, but are not limited to metabolic or physiologic function of compounds of SEQ ID NO:1 or derivatives thereof including similar activities or improved activities or those activities with decreased undesirable side-effects. Also included are antigenic and immunogenic activities of said compounds such as for example, SEQ ID NO:1 or derivatives thereof.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

DNA construct. As used herein, "DNA construct" should be understood to refer to a recombinant, man-made DNA, either linear or circular.

Derivative or Functional Derivative: The term "derivative" or "functional derivative" is intended to include "variants," the "derivatives," or "chemical derivatives" of the PTH molecule. A "variant" of a molecule such as for example, a compound of SEQ ID NO:1 or derivative thereof is meant to refer to a molecule substantially similar to either the entire molecule, or a fragment thereof. An "analog" of a molecule such as for example, a compound of SEQ ID NO:1 or derivative thereof is meant to refer to a non-natural molecule substantially similar to either the SEQ ID NO:1 molecules or fragments thereof.

PTH derivatives contain changes in the polypeptide relative to the native PTH polypeptide of the same size. The sequence of the native PTH(1-14) polypeptide is that of SEQ. ID NO:14 (human) or 17 (rat). A molecule is said to be "substantially similar" to another molecule if the sequence of amino acids in both molecules is substantially the same, and if both molecules possess a similar biological activity. Thus, two molecules that possess a similar activity, may be considered variants, derivatives, or analogs as that term is used herein even if one of the molecules contains additional amino acid residues not found in the other, or if the sequence of amino acid residues is not identical. PTH derivatives, however, need not have substantially similar biological activity to the native molecule. In some instances PTH derivatives may have substantially different activity than the native PTH. For example, a derivative may be either an antagonist or an agonist of the PTH receptor.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Expression vector. As used herein, an "expression vector" is a DNA construct that contains a structural gene operably linked to an expression control sequence so that the structural gene can be expressed when the expression vector is transformed into an appropriate host cell. Two DNA sequences are said to be "operably linked" if the biological activity of one region will affect the other region and also if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that desired DNA sequence.

Fragment: A "fragment" of a molecule such as for example, SEQ ID NO: 1 or derivative thereof is meant to refer to any polypeptide subset of these molecules.

Fusion protein: By the term "fusion protein" is intended a fused protein comprising compounds such as for example, SEQ ID NO:1 or derivatives thereof, either with or without a "selective cleavage site" linked at its N-terminus, which is in turn linked to an additional amino acid leader polypeptide sequence.

Gene therapy. As used herein, "gene therapy" means, inter alia, the ability to ameliorate, eliminate or attenuate a defect or disease by altering a gene of interest or the product expressed by the gene of interest, by altering the genotype of the cell or organism of interest or by altering the normal pattern of gene expression of an organism. For example, this may be accomplished by replacing the gene of interest with a mutated gene, knocking out the gene of interest or inserting a different gene that produces a product that inhibits or stimulates the gene of interest or using other methods known to those of skill in the art. Generally, a recombinant polynucleotide is introduced into cells or tissues of an organism to effect a change in gene expression. The manipulation of the genetic material may be accomplished either in vivo or ex vivo. The above examples are not meant to limit the different ways in which the gene therapy may be effected. Any techniques known to those of skill in the art of gene therapy may be used with the claimed invention.

Host Animal: The term transgenic animals refers to those animals whose germ and somatic cells contain a DNA construct of the invention. Such transgenic animals are in general vertebrates. Preferred host animals are mammals such as non-human primates, mice, sheep, pigs, cattle, goats, guinea pigs, rodents, e.g. rats, and the like. The term "host animal" also includes animals in all stages of development, including embryonic and fetal stages.

% Identity: Whether any two polypeptides or polynucleotides are for example, at least 90% "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database may be used to determine identity The terms homology and identity are often used interchangeably. In this regard, percent homology or identity may be determined by methods known to those of skill in the art. For example, by comparing sequence information using a GAP computer program, version 6.0, available from the University of Wisconsin Genetics Computer Group (UWGCG). The GAP program utilizes the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences.

In general, sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(i):387 (1984)), BLASTP, BLASTN, FASTA (Atschul, S. F., et al., *J Molec Biol* 215:403 (1990)).

Therefore, as used herein, the term "identity" represents a comparison between a test and a reference polypeptide or polynucleotide. More specifically, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids, that no more than 10% (i.e., 10 out of 100) amino acids in the test polypeptides differ from that of the reference polypeptides. Such differences may be represented as point mutations randomly distributed over the entire length of the amino acid sequence of the invention or they may be clustered in one or more locations of varying length up to the maximum allowable, e.g. $1/14$ amino acid difference (approximately 90% identity). Differences are defined as amino acid substitutions, or deletions.

An example of the determination of relative identity between different polypeptides is shown in Table 1.

TABLE 1

Sequence identity compared to native rPTH(1-14)

| Peptide | | # Identity |
|---|---|---|
| rPTH(1-14): | AVSEIQLMHNLGKH | 100 |
| #1: | AVAEIQLMHARAKH | 71.4 |
| #2: | AVEIQLMHARAKW | 64.3 |
| #3: | AVAEIQLMHQRAKH | 71.4 |
| #4: | AVAEIQLMHARAK | 64.3 |
| #5: | AVAEIQLMHARA | 57.1 |
| #6: | AVAEIQLMHAR | 57.1 |
| #7: | AVAEIQLMHARAKHLNSMERVEWLRKKLQDVHNY | 29.4 |

% Identity was calculated by the William Pearson's lalign program. The lalign program implements the algorithmof Huang and Miller, published in Adv. Appl. Meth. 12: 337-357 (1991). The program is part of the FASTA packageof sequence analysis program. The global alignment method with default parameters (BLOSUM50, gap penalties: −14/−4)was used. See http://www.ch.embnet.org/software/LALIGN_form.html)

Isolated: A term meaning altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of compounds of for example SEQ ID NO:1 and derivatives thereof can be substantially purified by the one-step method described in Smith and Johnson, *Gene* 67:31-40 (1988). The terms isolated and purified are sometimes used interchangeably.

By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a native DNA sequence encoding compounds of for example, SEQ ID NO:1 and derivatives thereof, or may differ from such sequence by the deletion, addition, or substitution of one or more nucleotides. Single-stranded DNAs of the invention are generally at least 8 nucleotides long, (preferably at least 18 nucleotides long, and more preferably at least 30 nucleotides long) ranging up to full length of the DNA molecule encoding compounds of SEQ ID NO:1 and derivatives thereof (i.e., 42 nucleotides); they preferably are detectably labeled for use as hybridization probes, and may be antisense.

Isolated or purified as it refers to preparations made from biological cells or hosts should be understood to mean any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange change chromatography, affinity chromatography, density gradient centrifugation and electrophoresis.

A preparation of DNA or protein that is "pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

Leader Sequence: By the term "leader sequence" is intended a polynucleotide sequence linked to compounds of for example, SEQ ID NO:1, and expressed in host cells as a fusion protein fused to the selective cleavage site and compounds of SEQ ID NO:1. The term "leader polypeptide" describes the expressed form of the "leader sequence" as obtained in the fusion protein.

The fusion protein, which is often insoluble and found in inclusion bodies when it is overexpressed, is purified from other bacterial protein by methods well known in the art. In a preferred embodiment, the insoluble fusion protein is centrifuged and washed after cell lysis, and resolubilized with guanidine-HCl. It can remain soluble after removal of the denaturant by dialysis. (For purification of refractile proteins, see Jones, U.S. Pat. No. 4,512,922; Olson, U.S. Pat. No. 4,518,526; and Builder et al., U.S. Pat. Nos. 4,511,502 and 4,620,948).

The recombinantly produced compounds of for example, SEQ ID NO:1 or derivatives thereof can be purified to be substantially free of natural contaminants from the solubilized fusion protein through the use of any of a variety of methodologies. As used herein, a compound is said to be "substantially free of natural contaminants" if it has been substantially purified from materials with which it is found following expression in bacterial or eukaryotic host cells. Compounds of SEQ ID NO:1 or derivatives thereof may be purified through application of standard chromatographic separation technology.

Alternatively, the peptide may be purified using immunoaffinity chromatography (Rotman, A. et al., *Biochim. Biophys. Acta* 641:114-121 (1981); Sairam, M. R. J,. *Chromatog* 215:143-152 (1981); Nielsen, L. S. et al., *Biochemistry* 21:6410-6415 (1982); Vockley, J. et al., *Bio-* chem. *J.* 217:535-542 (1984); Paucha, E. et al., *J. Virol.* 51:670-681 (1984); and Chong, P. et al., *J. Virol. Meth.* 10:261-268 (1985)).

After partial or substantial purification, the fusion protein is treated enzymatically with the enzyme corresponding to the cleavage site. Alternatively, the fusion protein in its more impure state, even in refractile form, can be treated with the enzyme. If needed, the resulting mature compounds of for example, SEQ ID NO:1 or derivatives thereof, can be further purified. Conditions for enzymatic treatment are known to those of skill in the art.

Operably Linked: Two DNA sequences (such as a promoter region sequence and a sequence encoding a PTH derivative) are said to be operably linked if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that DNA sequence.

Polynucleotide: This term generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: Polypeptide and peptide are used interchangeably. The term polypeptide refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids and include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translational modifications or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties,* 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors", *Methods in Enzymol.* 182: 626-646 (1990) and Rattan et al., "Protein Synthesis: Posttranslational Modifications and Aging", *Ann NY Acad Sci* 663:48-62 (1992).

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Examples of promoters include the CMV promoter (InVitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). Also, tissue-specific enhancer elements may be employed. Additionally, such promoters may include tissue and cell-specific promoters of an organsim.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Selective cleavage site: The term "selective cleavage site" refers to an amino acid residue or residues which can be selectively cleaved with either chemicals or enzymes in a predictable manner. A selective enzyme cleavage site is an amino acid or a peptide sequence which is recognized and hydrolyzed by a proteolytic enzyme. Examples of such sites include, without limitation, trypsin or chymotrypsin cleavage sites.

Stringent Hybridization. As used herein "stringent hybridization" conditions should be understood to be those conditions normally used by one of skill in the art to establish at least a 95% homology between complementary pieces of DNA or DNA and RNA.

There are only three requirements for hybridization to a denatured strand of DNA to occur. (1) There must be complementary single strands in the sample. (2) The ionic strength of the solution of single-stranded DNA must be fairly high so that the bases can approach one another; operationally, this means greater than 0.2M. (3) The DNA concentration must be high enough for intermolecular collisions to occur at a reasonable frequency. The third condition only affects the rate, not whether renaturation/hybridization will occur.

Conditions routinely used by those of skill in the art are set out in readily available procedure texts, e.g., Ausubel. F. et al., *Current Protocols in Molecular Biology*, Vol. 1, Chap. 2.10, John Wiley & Sons, Publishers (1994) or Sambrook et al., *Molecular Cloning*, Cold Spring Harbor (1989), the entire documents incorporated herein by reference. As would be known by one of skill in the art, the ultimate hybridization stringency reflects both the actual hybridization conditions as well as the washing conditions following the hybridization, and one of skill in the art would know the appropriate manner in which to change these conditions to obtain a desired result.

For example, a prehybridization solution should contain sufficient salt and nonspecific DNA to allow for hybridization to non-specific sites on the solid matrix, at the desired temperature and in the desired prehybridization time. For example, for stringent hybridization, such prehybridization solution could contain 6× sodium chloride/sodium citrate (1×SSC is 0.15 M NaCl, 0.015 M Na citrate; pH 7.0), 5× Denhardt's solution, 0.05% sodium pyrophosphate and 100 µg per ml of herring sperm DNA. An appropriate stringent hybridization mixture might then contain 6×SSC, 1× Denhardt's solution, 100 µg per ml of yeast tRNA and 0.05% sodium pyrophosphate.

Alternative conditions for DNA-DNA analysis could entail the following:
1) prehybridization at room temperature and hybridization at 68° C.;
2) washing with 0.2×SSC/0.1% SDS at room temperature;
3) as desired, additional washes at 0.2×SSC/0.1% SDS at 42° C. (moderate-stringency wash); or
4) as desired, additional washes at 0.1×SSC/0.1% SDS at 68° C. (high stringency).

Known hybridization mixtures, e.g., that of Church and Gilbert, *Proc. Natl. Acad. Sci. USA* 81:1991-1995 (1984), comprising the following composition may also be used: 1% crystalline grade bovine serum albumin/1 mM EDTA/0.5M NaHPO$_4$, pH 7.2/7% SDS. Additionally, alternative but similar reaction conditions can also be found in Sambrook et al., *Molecular Cloning*, Cold Spring Harbor (1989). Formamide may also be included in prehybridization/hybridization solutions as desired. The invention may include DNA sequences that stringently hybridize to nucleic acid sequences encoding PT derivatiaves.

Transgenic. As used herein, a "transgenic" organism is an organism containing a transgene, wherein the transgene was introduced into the organism or an ancestor of the organism at a prenatal stage, e.g., an embryonic stage. The transgene results in a defined change to its germ line, wherein the change is not ordinarily found in wild-type organisms. This change can be passed on to the organism's progeny and therefore the progeny are also transgenic animals. The change to the organism's germ line can be an insertion, a substitution, or a deletion in the gene of interest. Non-human animals are organisms into which transgenes may be introduced by techniques known in the art, such animals include but are not limited to mice, goats, sheep, pigs, cows and other domestic farm animals. Methods for generating transgenic animals have become convention in the art and are described, for example, in Hogan B. et al., "A Laboratory Manual, Cold Spring Harbor, N.Y. (1986) or U.S. Pat. No. 5,922,927 or 5,917,123. A transgenic animal that carries one transgene can be further bred to another transgenic animal carrying a second transgene to create a "double transgenic" animal carrying two transgenes.

It should be understood that these conditions are not meant to be definitive or limiting and may be adjusted as required by those of ordinary skill in the art to accomplish the desired objective.

Compounds of the Invention—Structural and Functional Properties

Described herein are novel "minimized" variants of PTH that are small enough to be deliverable by simple non-injection methods. Also described are larger PTH derivatives having substitutions in the first 14 amino acids of the polypeptide. The new polypeptides correspond to the 1-34, 1-32, 1-30, 1-28, 1-26, 1-24, 1-22, 1-20, 1-14, 1-13, 1-12, 1-11, 1-10 and 1-9 amino acid sequence of native PTH. The shorter variants (≦PTH 1-14) have a molecular weight of less than 2,000 daltons.

The primary amino acid sequence of the native human PTH(1-14) peptide (N-terminus to C-terminus) is SerValSerGluIleGlnLeuMetHisAsnLeuGlyLysHis (SEQ ID NO: 14), whereas the primary amino acid sequence of the native PTHrP(1-14) peptide (N-terminus to C-terminus) is AlaValSerGluHisGlnLeuLeu HisAspLysGlyLysSer (SEQ ID NO:15).

Frequently in this section, reference is made to the polypeptide of SEQ ID NO:1. This is merely illustrative and should not be meant to imply that this is limiting in any way relative to the other polypeptide sequences of the invention. As protein products, compounds of the invention are amenable to production by the techniques of solution- or solid-phase peptide synthesis or recombinant biology.

The solid phase peptide synthesis technique, in particular, has been successfully applied in the production of human PTH and can be used for the production of compounds of SEQ ID NO:1 pr derivatives thereof (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991), incorporated herein by reference. The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC-or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of such as for example, SEQ ID NO: 1 and derivatives thereof which incorporate amino acids that are not genetically encoded, such as homoarginine.

In one aspect of the invention, any amino-acid substitutions at positions 1-9, and more particularly those amino acid substitutions at amino acid positions 10, 11, 12, 14, and/or 19, which do not destroy the biological activity of the PTH polypeptide to antagonize or agonize the PTH-1/PTH-2 receptor (as determined by assays known to the skilled artisan and discussed herein), are also included within the scope of the present invention.

The synthetic analog of bovine PTH, PTH(3-34) has been recognized as a potent PTH antagonist in vitro. Variants of PTH lacking N-terminal amino acids 1-2 and 1-7, were shown to be devoid of agonist activity and capable of antagonist activity (Born, W. et al., *Endocrinol.* 23:1848-1853 (1988)). Preferred potential antagonist variants of SEQ ID NO: 1 of this invention are variants truncated at the N-terminus.

When a variant is truncated by one amino acid at the N-terminus, it is termed PTH or PTHrP(2-14), in that it lacks amino acid residue #1 but contains amino acid residues #2-14. When a variant is truncated by one amino acid at the C-terminus, it is termed PTH or PTHrP(1-13), in that it lacks amino acid residue #14 but contains amino acid residues #1-13. This numbering system also applies to more truncated versions of PTH.

In accordance with another aspect of the present invention, substituents may be attached to the free amine of the N-terminal amino acid of compounds such as, for example, SEQ ID NO: 1 or derivatives thereof by standard methods known in the art. For example, alkyl groups, e.g., $C_{1-12}$ alkyl, may be attached using reductive alkylation. Hydroxyalkyl groups, e.g. $C_{1-12}$ hydroxyalkyl, may also be attached using reductive alkylation wherein the free hydroxy group is protected with a t-butyl ester. Acyl groups, e.g., $COE_1$, may be attached by coupling the free acid, e.g., $E_1COOH$, to the free amino of the N-terminal amino acid. Additionally, possible chemical modifications of the C-terminal end of the polypeptide are encompassed within the scope of the invention. These modifications may modify binding affinity to the receptor.

Also contemplated within the scope of this invention are those compounds such as for example, SEQ ID NO:1 and derivatives thereof that alter secondary or tertiary structure, or stability of compounds such as SEQ ID NO: 1 or derivatives thereof which still retain biological activity. Such derivatives might be achieved through lactam cyclization, disulfide bonds, or other means known to a person of ordinary skill in the art.

Vectors, Host Cells, and Recombinant Expression

The present invention also relates to vectors that comprise a polynucleotide of the present invention, and host cells which are genetically engineered with vectors of the invention and the production of polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., Molecular Cloning: A Laboratory Manual (supra).

RNA vectors may also be utilized for the expression of the nucleic acids encoding compounds of the invention or derivatives thereof disclosed in this invention. These vectors are based on positive or negative strand RNA viruses that naturally replicate in a wide variety of eukaryotic cells (Bredenbeek, P. J. & Rice, C. M., *Virology* 3: 297-310, 1992). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11:18-22, 1993; Frolov, I., et al., Proc. Natl. Acad. Sci. (USA) 93: 11371-11377, 1996). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

The expression of a DNA sequence requires that the DNA sequence be "operably linked" to DNA sequences which contain transcriptional and translational regulatory information. An operable linkage is a linkage in which the control or regulatory DNA sequences and the DNA sequence sought to be expressed are connected in such a way as to permit gene expression. The precise nature of the "control regions"

needed for gene expression may vary from organism to organism, but shall in general include a promoter region which, in prokaryotic cells, contains both the promoter (which directs the initiation of RNA transcription) as well as DNA sequences which, when transcribed into RNA, will signal the initiation of protein synthesis. Regulatory regions in eukaryotic cells will in general include a promoter region sufficient to direct the initiation of RNA synthesis.

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligates. In the case of a fusion protein, the genetic construct encodes an inducible promoter which is operably linked to the 5' gene sequence of the fusion protein to allow efficient expression of the fusion protein.

To express compounds of the invention or a derivative thereof in a prokaryotic cell (such as, for example, E. coli, B. subtilis, Pseudomonas, Streptomyces, etc.), it is necessary to operably link, for example, the SEQ ID NO: 1-encoding DNA sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage λ, (PL and PR), the trp, recA. lacZ. lacI. and gal promoters of E. coli, the α-amylase (Ulmanen, I. et al., J. Bacteriol. 162:176-182 (1985)), and the σ-28-specific promoters of B. subtilis (Gilman, M. Z. et al., Gene 32:11-20 (1984)), the promoters of the bacteriophages of Bacillius (Gryczan, T. J., In: The Molecular Biology of the Bacilli, Academic Press, Inc., NY (1982)), and Streptomyces promoters (Ward, J. M. et al., Mol. Gen. Genet. 203:468-478 (1986)). Prokaryotic promoters are reviewed by Glick, B. R., J. Ind. Microbiol. 1:277-282 (1987); Cenatiempo, Y., Biochimie 68:505-516 (1986)); and Gottesman, S., Ann. Rev. Genet. 18:415-442 (1984)).

The preferred prokaryotic promoter for this invention is the E. coli trp promoter, which is inducible with indole acrylic acid.

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Hamer, D. et al., J. Mol. Appl. Gen. 1:273-288 (1982)); the TK promoter of Herpes virus (McKnight, S., Cell 31:355-365 (1982)); the SV40 early promoter (Benoist, C., et al., Nature (London) 290:304-310 (1981)); and the yeast gal4 gene promoter (Johnston, S. A., et al., Proc. Natl. Acad. Sci. (USA) 79:6971-6975 (1982); Silver, P. A., et al., Proc. Natl. Acad. Sci. (USA) 81:5951-5955 (1984)).

Preferably, the introduced gene sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in E. coli (such as, for example, pBR322, ColEl, pSC101, pACYC 184, πVX. Such plasmids are, for example, disclosed by Maniatis, T., et al., In: Molecular Cloning, A Laboratory Manual, Cold Spring Harbor Press, Cold Spring Harbor, N.Y. (1982)). Preferred plasmid expression vectors include the pGFP-1 plasmid described in Gardella et al., J. Biol. Chem. 265:15854-15859 (1989), or a modified plasmid based upon one of the pET vectors described by Studier and Dunn, Methods in Enzymology 185:60-89 (1990). Bacillus plasmids include pC194, pC221, pT127, etc. Such plasmids are disclosed by Gryczan, T. In: The Molecular Biology of the Bacilli, Academic Press, NY pp. 307-329 (1982). Suitable Streptomyces plasmids include pIJIOI (Kendall, K. J. et al., J. Bacteriol. 169:4177-4183 (1987)), and streptomyces bacteriophages such as φC31 (Chater, K. F. et al., In: Sixth International Symposium on Actinomycetales Biology, Akademiai Kaido, Budapest, Hungary, pp. 45-54 (1986)). Pseudomonas plasmids are reviewed by John, J. F. et al., Rev. Infect. Dis. 8:693-704 (1986)), and Izaki, K., Jon. J. Bacteriol. 33:729-742 (1978)).

Preferred eukaryotic expression vectors include, without limitation, BPV, vaccinia, 2-micron circle etc. Such expression vectors are well known in the art (Botstein, D., et al., Miami Wntr. Symp. 19:265-274 (1982); Broach, J. R., In; The Molecular Biology of the Yeast Saccharomyces: Life Cycle and Inheritance, Cold Spring Harbor Laboratory, Cold Spring Harbor, N.Y. pp. 445-470 (1981); Broach, J. R., Cell 28:203-204 (1982); Bollon, D. P., et al., J. Clin. Hematol. Oncol. 10:3948 (1980); Maniatis, T., In: Cell Biology: A Comprehensive Treatise, Vol. 3, Gene Expression, Academic Press, NY, pp. 563-608 (1980)).

In addition to microorganisms, cultures of cells derived from multicellular organisms may also be used as hosts. In principle, any such cell culture is workable, whether from vertebrate or invertebrate cellular sources. Interest, however, has been greater with cells from vertebrate sources. Examples of useful vertebrate host cell lines are VERO and HeLa cells, Chinese hamster ovary (CHO) cell lines, W138, BHK, COS-7, and MDCK cell lines. Expression vectors for such cells ordinarily include (if necessary) an origin of replication, a promoter located in front of or upstream to the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Simian Virus 40 (SV40) and cytomegalovirus. The early and late promoters of SV40 virus are particularly useful because both are obtained easily from the virus as a fragment which also contains the SV40 vial origin of replication (Fiers et al., Nature 273:113 (1978)).

An origin of replication may be provided either by construction of the vector to include an exogenous origin, such as may be derived from SV40 or other viral (e.g. Polyoma, Adeno, VSV, BPV) source or may be provided by the host cell chromosomal replication mechanism. If the vector is integrated into the host cell chromosome, the latter is often sufficient.

If cells without formidable cell membrane barriers are used as host cells, transfection is carried out by the calcium phosphate precipitation method as described by Graham and Van der Erb, Virology 52:546 (1978). However, other methods for introducing DNA into cells, such as by nuclear injection or by protoplast fusion may also be used. In the case of gene therapy, the direct naked plasmid or viral DNA injection method, with or without transfection-facilitating agents such as, without limitation, liposomes, provides an alternative approach to the current methods of in vivo or in vitro transfection of mammalian cells. If prokaryotic cells or cells which contain substantial cell wall constructions are used, the preferred method of transfection is calcium treatment, using calcium chloride as described in Cohen et al., *Proc. Natl. Acad. Sci. USA* 69:2110 (1972).

Gene Therapy

A patient (human or non-human) suffering from symptoms of a disease such as osteoporosis or other diseases requiring PTH may be treated by gene therapy. By undertaking this approach, there should be an attenuation of the disease symptoms. Gene therapy has proven effective or has been considered to have promise in the treatment of certain forms of human hemophilia (Bontempo, F. A., et al., *Blood* 69:1721-1724 (1987); Palmer, T. D., et al., *Blood* 73:438-445 (1989); Axelrod, J. H., et al., *Proc. Natl. Acad. Sci. USA* 87:5173-5177 (1990); Armentano, D., et al., *Proc. Natl. Acad. Sci. USA* 87:6141-6145 (1990)), as well as in the treatment of other mammalian diseases such as cystic fibrosis (Drumm, M. L., et al., *Cell* 62:1227-1233 (1990); Gregory, R. J., et al., *Nature* 347:358-363 (1990); Rich, D. P., et al., *Nature* 347:358-363 (1990)), Gaucher disease (Sorge, J., et al., *Proc. Natl. Acad. Sci. USA* 84:906-909 (1987); Fink, J. K., et al., *Proc. Natl. Acad. Sci. USA* 87:2334-2338 (1990)), muscular dystrophy (Partridge, T. A., et al., *Nature* 337:176-179 (1989); Law, P. K., et al., *Lancet* 336:114-115 (1990); Morgan, J. E., et al., *J. Cell Biol.* 111:2437-2449 (1990)), and metastatic melanoma (Rosenberg, S. A., et al., *Science* 233:1318-1321 (1986); Rosenberg, S. A., et al., *N. Eng. J. Med.* 319:1676-1680 (1988); Rosenberg, S. A., et al., *N. Eng. J. Med.* 323:570-578 (1990)). More recently, gene therapy has been shown to provide anticancer or antitumor activity in patients with prostate cancer (Herman, J. R. et al., *Hum. Gene Ther.* 10:1239-1249 (1999) and metastatic melanoma (Nemunaitis, J. et al., *Hum. Gene Ther.* 20:1289-1298 (1999)). Additionally, several patents have issued to methods of gene therapy. For example, U.S. Pat. Nos. 5,836,905, 5,741,486, 5,871,486 and 5,656,465

In a preferred approach, a polynucleotide having the nucleotide sequence for the PTH polypeptide derivative may be incorporated into a vector suitable for introducing the nucleic acid molecule into cells of the mammal to be treated, to form a transfection vector.

A variety of vectors have been developed for gene delivery and possible gene therapy. Suitable vectors for this purpose include retroviruses, adenoviruses and adeno associated viruses (AAV). Alternatively, the nucleic acid molecules of the invention may be complexed into a molecular conjugate with a virus (e.g., an adenovirus) or with viral components (e.g., viral capsid proteins). The vectors derive from herpes simplex virus type 1 (HSV-1), adenovirus, adeno-associated virus (AAV) and retrovirus constructs (for review see Friedmann, T., *Trends Genet* 10:210-214 (1994); Jolly, D., *Cancer Gene Therapy* 1 (1994); Mulligan, R. C., *Science* 260:926-932 (1993); Smith, F. et al., *Rest. Neurol. Neurosci.* 8:21-34 (1995)). Vectors based on HSV-1, including both recombinant virus vectors and amplicon vectors, as well as adenovirus vectors can assume an extrachromosomal state in the cell nucleus and mediate limited, long term gene expression in postmitotic cells, but not in mitotic cells. HSV-1 amplicon vectors can be grown to relatively high titers ($10^7$ transducing units/ml) and have the capacity to accommodate large fragments of foreign DNA (at least 15 kb, with 10 concatemeric copies per virion). AAV vectors (rAAV), available in comparable titers to amplicon vectors, can deliver genes (<4.5 kb) to postmitotic, as well as mitotic cells in combination with adenovirus or herpes virus as helper virus. Long term transgene expression is achieved by replication and formation of "episomal" elements and/or through integration into the host cell genome at random or specific sites (for review see Samulski, R. J., *Current Opinion in Genetics and Development* 3:74-80 (1993); Muzyczka, N., *Curr. Top. Microbiol. Immunol.* 158:97-129 (1992)). HSV, adenovirus and rAAV vectors are all packaged in stable particles. Retrovirus vectors can accommodate 7-8 kb of foreign DNA and integrate into the host cell genome, but only in mitotic cells, and particles are relatively unstable with low titers. Recent studies have demonstrated that elements from different viruses can be combined to increase the delivery capacity of vectors. For example, incorporation of elements of the HIV virion, including the matrix protein and integrase, into retrovirus vectors allows transgene cassettes to enter the nucleus of non-mitotic, as well as mitotic cells and potentially to integrate into the genome of these cells (Naldini, L. et al., *Science* 272:263-267 (1996)); and inclusion of the vesicular somatitis virus envelope glycoprotein (VSV-G) increases stability of retrovirus particles (Emi, N. et al., *J. Virol.* 65:1202-1207 (1991)).

HSV-1 is a double-stranded DNA virus which is replicated and transcribed in the nucleus of the cell. HSV-1 has both a lytic and a latent cycle. HSV-1 has a wide host range, and infects many cell types in mammals and birds (including chicken, rat, mice monkey, and human) Spear et al., *DNA Tumor Viruses*, J. Tooze, Ed. (Cold Spring Harbor Laboratory, Cold Spring Harbor, N.Y., 1981, pp. 615-746). HSV-1 can lytically infect a wide variety of cells including neurons, fibroblasts and macrophages. In addition, HSV-1 infects post-mitotic neurons in adult animals and can be maintained indefinitely in a latent state. Stevens, *Current Topics in Microbiology and Immunology* 70:31(1975). Latent HSV-1 is capable of expressing genes.

AAV also has a broad host range and most human cells are thought to be injectable. The host range for integration is believed to be equally broad. AAV is a single stranded DNA parvovirus endogenous to the human population, making it a suitable gene therapy vector candidate. AAV is not associated with any disease, therefore making it safe for gene transfer applications (Cukor et al., The Parvoviruses, Ed. K. I. Berns, Plenum, N.Y., (1984) pp. 33-36; Ostrove et al., Virology 113: 521 (1981)). AAV integrates into the host genome upon infection so that transgenes can be expressed indefinitely (Kotin et al., Proc. Natl. Acad. Sci. USA 87: 221 (1990); Samulski et al., Embo J. 10: 3941 (1991)). Integration of AAV into the cellular genome is independent of cell replication which is particularly important since AAV can thus transfer genes into quiescent cells (Lebkowski et al., *Mol. Cell. Biol.* 8:3988 (1988)).

Both HSV and AAV can deliver genes to dividing and non-dividing cells. In general, HSV virions are considered more highly infectious that AAV virions, with a ratio of virus particles: infectious units in the range of 10 for HSV (Browne, H. et al., *J. Virol.* 70:4311-4316 (1996)) and up to thousands for AAV (Snyder, R. O. et al., In Current Protocols in Human Genetics, Eds. Dracopoli, N. et al., John Wiley and Sons: New York (1996), pp. 1-24), and both having a broad species range. Still, each virion has specific trophisms which will affect the efficiency of infection of specific cell types. The recent identification of a membrane receptor for HSV-1 which is a member of the tumor necrosis factor alpha family (Montgomery, R. I. et al., 21st Herpes Virus Workshop Abstract #167 (1996)) indicates that the distribution of this receptor will affect the relative infectability of cells, albeit most mammalian cell types appear to be injectable with HSV-1. AAV also has a very wide host and cell type range. The cellular receptor for AAV is not known, but a 150 kDA glycoprotein has been described whose presence in cultured cells correlates with their ability to bind AAV (Mizukami, H. et al., *Virology* 217:124-130 (1996)).

Techniques for the formation of such vectors are well-known in the art, and are generally described in "Working Toward Human Gene Therapy," Chapter 28 in *Recombinant DNA*, 2nd Ed., Watson, J. D. et al., eds., New York: Scientific American Books, pp. 567-581 (1992). In addition, general methods for construction of gene therapy vectors and the introduction thereof into affected animals for therapeutic purposes may be found in the above-referenced publications, the disclosures of which are specifically incorporated herein by reference in their entirety.

In one general method, vectors comprising polynucleotides encoding PTH derivative gene are directly introduced into the cells or tissues of the affected individual, preferably by injection, inhalation, ingestion or introduction into a mucous membrane via solution; such an approach is generally referred to as "in vivo" gene therapy. Alternatively, cells or tissues, e.g., hematopoietic cells from bone marrow, may be removed from the affected animal and placed into culture according to methods that are well-known to one of ordinary skill in the art; the vectors comprising the polynucleotides may then be introduced into these cells or tissues by any of the methods described generally above for introducing isolated polynucleotides into a cell or tissue, and, after a sufficient amount of time to allow incorporation of the polynucleotides, the cells or tissues may then be re-inserted into the affected animal or a second animal in need of treatment. Since the introduction of the DNA of interest is performed outside of the body of the affected animal, this approach is generally referred to as "ex vivo" gene therapy.

For both in vivo and ex vivo gene therapy, the polynucleotides of the invention may alternatively be operatively linked to a regulatory DNA sequence, which may be a heterologous regulatory DNA sequence, to form a genetic construct as described above. This genetic construct may then be inserted into a vector, which is then directly introduced into the affected animal in an in vivo gene therapy approach, or into the cells or tissues of the affected animal in an ex vivo approach. In another preferred embodiment, the genetic construct may be introduced into the cells or tissues of the animal, either in vivo or ex vivo, in a molecular conjugate with a virus (e.g., an adenovirus) or viral components (e.g., viral capsid proteins).

The above approaches result in (a) homologous recombination between the nucleic acid molecule and the defective gene in the cells of the affected animal; (b) random insertion of the gene into the host cell genome; or (c) incorporation of the gene into the nucleus of the cells where it may exist as an extrachromosomal genetic element. General descriptions of such methods and approaches to gene therapy may be found, for example, in U.S. Pat. No. 5,578,461; WO 94/12650; and WO 93/09222.

Alternatively, transfected host cells, which may be homologous or heterologous, may be encapsulated within a semi-permeable barrier device and implanted into the affected animal, allowing passage of for example the PTH polypeptide derivative into the tissues and circulation of the animal but preventing contact between the animal's immune system and the transfected cells (see WO 93/09222).

Utility and Administration of Compounds of the Invention

Compounds of the invention or derivatives thereof have multiple uses. These include, inter alia, agonists or antagonists of the PTH receptor, prevention and treatment of a variety of mammalian conditions manifested by loss of bone mass, diagnostic probes, antigens to prepare antibodies for use as diagnostic probes and even as molecular weight markers. Being able to specifically substitute one or more amino acids in the PTH polypeptide permits construction of specific molecular weight polypeptides as required.

In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are also indicated for the prophylaxis and therapeutic treatment of hypoparathyroidism; Finally, the compounds of this invention are indicated for use as agonists for fracture repair and as antagonists for hypercalcemia.

In general, compounds of for example, SEQ ID NO: 1 or derivatives thereof, or salts thereof, are administered in amounts between about 0.01 and 1 µg/kg body weight per day, preferably from about 0.07 to about 0.2 µg/kg body weight per day. For a 50 kg human female subject, the daily dose of biologically active compound is from about 0.5 to about 50 µgs, preferably from about 3.5 to about 10 µgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected compounds of the invention, the nature and severity of the condition being treated, and the physical condition and mental acuity of the recipient.

Representative preferred delivery regimens include, without limitation, oral, parenteral, subcutaneous, transcutaneous, intramuscular and intravenous, rectal, buccal (including sublingual), transdermal, and intranasal insufflation.

Pharmaceutically acceptable salts retain the desired biological activity of the compounds of the invention without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Pharmaceutically acceptable buffers include but are not limited to saline or phosphate buffered saline. Also included in these solutions may be acceptable preservative known to those of skill in the art.

A further aspect of the present invention relates to pharmaceutical compositions comprising as an active ingredient compounds of the invention or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189, incorporated by reference herein. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987, incorporated by reference herein.

Like PTH, the PTH variants may be administered in combination with other agents useful in treating a given clinical condition. When treating osteoporosis and other bone-related disorders for example, the PTH variants may be administered in conjunction with a dietary calcium supplement or with a vitamin D analog (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

Receptor-Signaling Activities of Compounds of the Invention or Derivatives Thereof A crucial step in the expression of hormonal action is the interaction of hormones with receptors on the plasma membrane surface of target cells. The formation of hormone-receptor complexes allows the transduction of extracellular signals into the cell to elicit a variety of biological responses.

Polypeptides of the invention may be screened for their agonistic or antagonistic properties using the cAMP accumulation assay. Cells expressing PTH-1 receptor on the cell surface are incubated with native PTH(1-84) for 5-60 minutes at 37° C., in the presence of 2 mM IBMX (3-isobutyl-1-methyl-xanthine, Sigma, St. Louis, Mo.). Cyclic AMP accumulation is measured by specific radio-immunoassay. A compound of the invention that competes with native PTH (1-84) or PTH(1-34) for binding to the PTH-1 receptor, and that inhibits the effect of native PTH(1-84) or PTH(1-34) on cAMP accumulation, is considered a competitive antagonist. Such a compound would be useful for treating hypercalcemia.

Conversely, a compound of the invention or a derivative thereof that does not compete with native PTH(1-84) or PTH(1-34) for binding to the PTH-1 receptor, but which still prevents native PTH(1-84) or PTH(1-34) activation of cAMP accumulation (presumably by blocking the receptor activation site) is considered a non-competitive antagonist. Such a compound would be useful for treating hypercalcemia.

A compound of the invention or a derivative thereof that competes with native PTH(1-84) or PTH(1-34)) for binding to the PTH-1 receptor, and which stimulates cAMP accumulation in the presence or absence of native PTH(1-84) or PTH(1-34) is a competitive agonist. A compound of the invention or a derivative thereof that does not compete with native PTH(1-84) or PTH(1-34) for binding to the PTH-1 receptor but which is still capable of stimulating cAMP accumulation in the presence or absence of native PTH(1-84) or PTH(1-34), or which stimulates a higher cAMP accumulation than that observed by a compound of the invention or a derivative thereof alone, would be considered a non-competitive agonist.

Likewise, polypeptides of the invention may be screened for their agonistic or antagonistic properties using the inositol phosphate accumulation assay. Cells expressing PTH-1 receptor on the cell surface are incubated with native PTH (1-84), and inositol phosphate accumulation is measured by specific radio-immunoassay. A compound of the invention that competes with native PTH(1-84) or PTH(1-34) for binding to the PTH-1 receptor, and that inhibits the effect of native PTH(1-84) or PTH(1-34) on inositol phosphate accumulation, is considered a competitive antagonist. Such a compound would be useful for treating hypercalcemia.

Conversely, a compound of the invention or a derivative thereof that does not compete with native PTH(1-84) or PTH(1-34) for binding to the PTH-1 receptor, but which still prevents native PTH(1-84) or PTH(1-34) activation of inositol phosphate accumulation (presumably by blocking the receptor activation site) is considered a non-competitive antagonist. Such a compound would be useful for treating hypercalcemia.

A compound of the invention or a derivative thereof that competes with native PTH(1-84) or PTH(1-34)) for binding to the PTH-1 receptor, and which stimulates inositol phosphate accumulation in the presence or absence of native PTH(1-84) or PTH(1-34) is a competitive agonist. A compound of the invention or a derivative thereof that does not compete with native PTH(1-84) or PTH(1-34) for binding to the PTH-1 receptor but which is still capable of stimulating inositol phosphate accumulation in the presence or absence of native PTH(1-84) or PTH(1-34), or which stimulates a higher inositol phosphate accumulation than that observed by a compound of the invention or a derivative thereof alone, would be considered a non-competitive agonist.

Therapeutic Uses of Compounds of the Invention or Derivatives Thereof

Some forms of hypercalcemia and hypocalcemia are related to the interaction between PTH and PTHrP and the PTH-1 and PTH-2 receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

Nucleic acids of the invention or derivatives thereof may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of compounds of the invention or derivatives thereof in selected tissues (e.g., the osteocalcin promoter for bone). Such promoters are used to direct tissue-specific expression of compounds of the invention or derivatives thereof in the transgenic animal.

In addition, any other amino-acid substitutions of a nature, which do not destroy the ability of the PTH derivative to antagonize or agonize the PTH-1/PTH-2 receptor (as determined by assays known to the skilled artisan and discussed below) are included in the scope of the present invention.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient therapeutically effective amount of a compound of the invention or a derivative thereof sufficient to inhibit activation of the PTH-1 receptor of said patient.

In this embodiment, a patient who is suspected of having a disorder resulting from altered action of the PTH-1 receptor may be treated using compounds of the invention or derivatives thereof of the invention which are a selective antagonists of the PTH-1 receptor. Such antagonists include compounds of the invention or derivatives thereof of the invention which have been determined (by the assays described herein) to interfere with PTH-1 receptor-mediated cell activation or other derivatives having similar properties.

To administer the antagonist, the appropriate compound of the invention or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of the invention or a derivative thereof binding to the PTH-1 receptor. Typical dosage would be 1 ng to 10 mg of the peptide per kg body weight per day.

In accordance with yet a further aspect of the invention, there is provided a method for treating osteoporosis, comprising administering to a patient a therapeutically effective amount of a compound of The invention or a derivative thereof, sufficient to activate the PTH-1 receptor of said patient. Similar dosages and administration as described above for the PTH/PTHrP antagonist, may be used for administration of a PTH/PTHrP agonist, e.g., for treatment of conditions such as osteoporosis, other metabolic bone disorders, and hypoparathyroidism and related disorders.

It will be appreciated to those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

INTRODUCTION TO THE EXAMPLES

High affinity binding of parathyroid hormone to the type-1 PTH receptor (PTH-1 receptor) and the subsequent induction of receptor activation involves multiple sites of ligand-receptor interaction. The analysis of peptide fragments of varying length broadly defined the regions within the fully active PTH(1-34) molecule that contain the major determinants of receptor binding affinity and cAMP-stimulating potency (Nussbaum, S. R., et al., *J. Biol. Chem.* 255:10183-10187 (1980); Rosenblatt, M., et al., *Endocrinology* 107:545-550 (1980); Tregear, G. W., et al., *Endocrinology* 93:1349-1353 (1973)). These studies mapped the functionalities to the C-terminal and N-terminal portions of the peptide, respectively. Deletions of the N-terminal residues, particularly, residues 1-6, result in peptides that bind efficiently to the receptor but fail to stimulate cAMP production, and thus provided the basis for the development of most PTH-1 receptor antagonists (Horiuchi, N., et al., *Science* 220:1053-1055 (1983)). Deletions from the C-terminal end of PTH(1-34) result in peptides that fail to bind detectably to the receptor, and short fragments containing only the C-terminal residues {e.g. PTH(15-34)} bind weakly to the receptor ($k_D$~-4 M), but are inactive in cAMP response assays (Caulfield, M. P., et al., *Endocrinology* 127:83-87 (1990); Abou-Samra, A.-B., et al., *Endocrinology* 125:2215-2217 (1989)). In contrast, fragments containing only the N-terminal residues and shorter in length than PTH(1-27) were previously found to be inactive in either receptor-binding or signaling assays (Nussbaum, S. R., et al., *J. Biol. Chem.* 255:10183-10187 (1980); Rosenblatt, M. (1981) in *Pathobiology Annual*, Vol. 11, Ioachim, H. L., ed., Raven Press, New York (1981), pp. 53-58).

The PTH-1 receptor is a class II G protein-coupled receptor that, upon agonist activation, strongly stimulates the adenylyl cyclase protein kinase A signaling pathway (Segre, G. V., & Goldring, S. R., *Trends in Endo. Metab.* 4:309-314 (1993); Kolakowski, L. F., *Receptors & Channels* 2:1-7 (1994); Jüppner, H., et al., *Science* 254:1024-1026 (1991)). The large amino-terminal extracellular domain of the receptor (~167 amino acids) is thought to provide the principal binding or docking site for the C-terminal portions of PTH(1-34), whereas the portion of the receptor containing the seven transmembrane domains and extracellular loops is thought to interact with the N-terminal signaling portion of the ligand (Mannstadt, M., et al., *J. Biol. Chem.* 273:16890-16896 (1998); Bergwitz, C., et al., *J. Biol. Chem.* 272: 28861-28868 (1997); Hoare, S., et al., *J. Pharmacol. Exp. Ther.* 289:1323-1333 (1999)). This bipartite scheme for PTH-PTH receptor interaction is supported by a considerable body of data from both mutational and crosslinking studies (Bergwitz, C., et al., *J. Biol. Chem.* 272:28861-28868 (1997); Bergwitz, C., et al., *J. Biol. Chem.* 271: 26469-26472 (1996); Bisello, A., et al., *J. Biol. Chem.* 273:22498-22565 (1998)) and is likely to hold true for other class II receptors (Dong, M., et al., *J. Biol. Chem.* 274:903-909 (1999); Holtmann, M., et al., *J. Biol. Chem.* 270:14394-14398 (1995); Holtmann, M. H., et. al., *J. Pharmacol. Exp Ther.* 279:555-560 (1996); Stroop, S., et al., *Biochem.* 34:1050-1057 (1995)). Nevertheless, this scheme is best viewed as a gross simplification of what is likely to be a complex problem involving a large network of interactions that in toto determines full agonist binding affinity and signaling potency.

Because of the important roles that the PTH-1 receptor and its two agonists, PTH and PTH-related peptide play in calcium homeostasis and bone development (Kronenberg, H., et al., in *Genetics of Endocrine and Metabolic disorders*, Thakker, R., ed., Chapman & Hall, London (1997), pp. 389-420), and the knowledge that PTH and PTHrP have anabolic effects on bone (Dempster, D. W., et al., *Endocr. Rev.* 14:690-709 (1993); Dempster, D. W., et al., (published erratum), *Endocr. Rev.* 15:261 (1994); Roe, E., et al., *J Bone Mineral Res.* 14 (Suppl. 1):S137 (1999); Plotkin, H., et al., *J. Clin. Endocrinol. & Metabol.* 83:2786-2791 (1998)), there is considerable interest in developing PTH-1 receptor agonists as therapeutics for bone diseases such as osteoporosis. A peptide such as PTH(1-34) is not ideal for therapeutic purposes because its large size is not suitable for non parenteral routes of delivery. Moreover, peptide molecules much larger in size than 5 amino acids are not suitable as starting points in rational drug design strategies aimed at developing peptido-mimetics. However, a strategy in which the minimum chain length of native PTH required for receptor activation is determined, and then subsequently optimized and further reduced in size could potentially lead to new low molecular weight PTH-1 receptor agonists. For a few moderately-sized peptide hormones, such iterative strategies of minimization and optimization have proven to be successful in developing "mimetic" peptide agonists that are much smaller than the parent hormone (Kimura, T., et al., *J. Biochem.* 122:1046-1051 (1997); Cwirla, S. E., et al., *Science* 276:1696-1699 (1997); Wells, J. A., *Science* 273: 449-450 (1996); Wrighton, N. C., et al., *Science* 273:458-464 (1996); Livnah, O., et al., *Science* 273:464-471 (1996); Li, B., et al., *Science* 270:1657-1660 (1995)).

It was recently found that in transfected cells expressing high levels of the PTH-1 receptor, weak cAMP-signaling activity could be detected for an N-terminal peptide as short as PTH(1-14) (Luck, M., et al., *Molecular Endocrinology* 13:670-680 (1999)).

The relative weak activity of this peptide can be reconciled by the absence of the C-terminal portion of PTH (1-34) that is known to contain important receptor-binding residues that serve to anchor the hormone to the receptor, most likely by "docking" to the amino-terminal domain of the receptor. This notion is supported by the observation that PTH(1-14) was as potent with a truncated rat PTH receptor that lacked the N-terminal extracellular domain as it was with the intact rPTH-1 receptor, whereas, in contrast, PTH(1-34) was 1000-fold weaker with the truncated receptor than it was with the intact receptor (Luck, M., et al., *Molecular Endocrinology* 13:670-680 (1999)). These findings, the strong deleterious effects on activation that result from deleting the N-terminal residues, and the high evolutionary conservation of these amino acids, predict that short N-terminal PTH peptides should interact productively with the receptor, and furthermore, if receptor binding affinity could be improved, then such peptides could be fully potent agonists.

The side chain requirements for receptor activation in PTH(1-14) thus use this peptide as a starting scaffold for identifying new modifications that i) enhance agonist activity with the PTH-1 receptor; ii) enable further reductions in peptide size and iii) function as probes of the ligand-receptor interaction mechanism was studied. The results show that the potency of PTH(1-14) can be significantly improved by several modifications, and that these enhancements are due to interactions with the portion of the receptor containing the seven transmembrane domains and extracellular loops.

Example 1

Single Substitutions of Amino Acids in PTH(1-14)

The effect of single amino acid substitutions in PTH(1-14) was initially studied. Various methods used in these studies are described below.

Polypeptides

All polypeptides in this study contained a carboxy-terminal amide. All analogs of rat (r)PTH(1-14)NH$_2$ {PTH(1-14)} and shorter length PTH peptides were synthesized on a multiple peptide synthesizer (Advanced Chemtech Model 396 MBS) using N-(9-fluorenyl)methoxycarbonyl (Fmoc) protecting group chemistry and TFA-mediated cleavage/ deprotection (MGH Biopolymer Synthesis Facility, Boston, Mass.); and desalted by adsorption on a C18-containing cartridge (Sep-Pak). [Tyr$^{34}$]human (h)PTH(1-34)NH$_2$ {(hPTH(1-34)} and [Nle$^{8,21}$,Tyr$^{34}$]-rPTH(1-34)NH$_2$ {rPTH (1-34)} were prepared on an Applied Biosystems model 431A peptide synthesizer using the same Fmoc chemistry and TFA-mediated cleavage/deprotection; followed by high performance liquid chromatography (HPLC). All peptides were reconstituted in 10 mM acetic acid, and stored at −80° C. The purity, identity, and stock concentration of each compound was secured by analytical HPLC, MALDI mass spectrometry, and amino acid analysis.

Cell Culture

Cells were cultured at 37° C. in T-75 flasks (75 mm$^2$) in Dulbecco's modified Eagle's medium (DMEM) supplemented with fetal bovine serum (10%), penicillin G (20 units/ml), streptomycin sulfate (20 µg/ml) and amphotericin B (0.05 µg/ml) in a humidified atmosphere containing 5% $CO_2$ Stock solutions of EGTA/trypsin and antibiotics were from GIBCO; fetal bovine serum was from Hyclone Laboratories (Logan, Utah). Cells were sub-cultured in 24-well plates and, when confluent, were treated with fresh media and shifted to 33° C. for 12 to 24 h prior to the assay (Bergwitz, C., et al., *J. Biol. Chem.* 272:28861-28868 (1997); Abell, A., et al., *J. Biol. Chem.* 271:4518-4527 (1996)).

Stably transfected derivatives of the porcine kidney cell line LLC-PK$_1$, HKRK-B7 (Takasu, H., et al., *J Bone Miner. Res.* 14:11-20 (1999)) and hPR2-20, express the human PTH-1 and human PTH-2 receptors respectively. The HKRK-B7 LLC-PK$_1$ cell line expresses the hPTH-1 receptor at ~1×10$^6$ receptors/cell (Takasu, H., et al., *J. Bone Miner. Res.* 14:11-20 (1999)), and the hPR2-22 LLC-PK$_1$ cell line expresses the hPTH-2 receptor at ~0.8×10$^6$ receptors/cell (provided by H. Takasu and F. R. Bringhurst, Endocrine Unit, Massachusetts General Hospital).

The rat osteoblastic cell line ROS 17/2.8 (Majeska, R. J., et al, *Endocrinology* 107:1494-1503 (1980)) expresses endogenous PTH-1 receptors at levels of ~80,000 per cell and the human osteoblastic cell line, SAOS-2, express endogenous PTH-1 receptors at levels of ~30,000 per cell.

Receptor Mutagenesis

The truncated receptor, referred to herein as hCNt, or hDelNt, was constructed by oligonucleotide-directed mutagenesis (Kunkel, T. A., *Proc. Natl. Acad. Sci. USA* 82:488-492 (1985)) using a mutagenic primer and single-stranded uracil-containing template DNA derived from HK-WT. This mutant receptor is deleted for residues 24 to 181 and, assuming that signal peptidase cleavage occurs between Ala$^{22}$ and Tyr$^3$ (Nielsen, H., et al., *Protein Engineering* 10:1-6 (1997)), is predicted to have Tyr$^3$ as its N-terminal residue joined to Glu$^{182}$ located at or near the boundary of the first transmembrane domain. A similar truncated rat PTH receptor was reported by us recently (Luck, M., et al., *Molecular Endocrinology* 13:670-680 (1999)). The DNA sequences of the mutant plasmid were verified in an ~600 nucleotide region spanning the mutation site using the Applied Biosystems Taq DyeDeoxy Terminator cycle sequencing method, with sample analysis being performed on an ABI 377 PRISM automated sequencer.

COS-7 Cells and DNA Transfection

Transient transfections of COS-7 cells with plasmids derived from the vector pcDNA-1 (InVitrogen, San Diego, Calif.) encoding the intact hPTH-1 receptor (HK-WT) (Schipani, E., et al., *Endocrinology* 132:2157-2165 (1993)), or the truncated human PTH-1 receptor, hΔNt, were performed using DEAE-dextran as described previously (Bergwitz, C., et al., *J. Biol. Chem.* 272:28861-28868 (1997)). COS-7 cells were transfected in 24-well plates when the cells were 85 to 95% of confluency using 200 ng of plasmid DNA that was purified by cesium chloride/ethidium bromide gradient centrifugation for each well. Assays were conducted 72 to 96 hours after transfection. Under these conditions about ~20% of the COS-7 cells become transfected and express about 5×10$^6$ intact surface PTH receptors per cell at the time of assay (Bergwitz, C., et al., *J. Biol. Chem.* 272:28861-28868 (1997)).

cAMP Stimulation

Stimulation of cells with peptide analogs was performed in 24-well plates. Cells were rinsed with 0.5 mL of binding buffer and treated with 200 µL of cAMP assay buffer (Dulbecco's modified Eagle's medium containing 2 mM 3-isobutyl-1-methylxanthine, 1 mg/mL bovine serum albumin, 35 mM Hepes-NaOH, pH 7.4) and 100 µL of binding buffer containing varying amounts of peptide analog (final volume=300 µL). The medium was removed after incubation for 1 h at room temperature, and the cells were frozen (−80° C.), lysed with 0.5 mL 50 mM HCl, and refrozen (−80° C.). The cAMP content of the diluted lysate was determined by radioimmunoassay. Where possible, cAMP $EC_{50}$ and Maximum response values were determined using nonlinear regression (see below).

Intracellular cAMP accumulation may be measured as described by Abou-Samra et al., *J. Biol. Chem.* 262:1129, 1986) or other methods known to those of skill in the art. Intracellular cAMP is extracted by thawing the cells in 1 ml of 50 mM HCl and analyzed by a specific radioimmunoassay using an anti-cAMP antibody (e.g., Sigma, St. Louis, Mo). A cAMP analog (2'-O-monosuccinyl-adenosine 3':5'-cyclic monophosphate tyrosyl methyl ester, obtained from Sigma) which is used as a tracer for cAMP is iodinated by the chloramine T method. Free iodine is removed by adsorbing the iodinated cAMP analog onto a C18 Sep-pak cartridge (Waters, Milford, Mass.). After washing with dH$_2$O, the iodinated cAMP analog is eluted from the Sep-pak Cartridge with 40% acetonitrille (ACN) and 0.1% trifluoroacetic acid (TFA). The iodinated cAMP analog is lyophilized, reconstituted in 1 ml 0.1% TFA, and injected into a C18 reverse phase HPLC column (Waters). The column is equilibrated with 10% ACN in 0.1% TFA, and eluted with gradient of 10-30% ACN in 0.1% TFA. This allows separation of the mono-iodinated cAMP analog from the non-iodinated cAMP analog. The tracer is stable for up to 4 months when stored at −20° C. The standard used for the assay, adenosine 3':5'-cyclic monophosphate, is purchased from Sigma. Samples (1-10 82 1 of HCl extracts) or standards (0.04-100 fmol/tube) are diluted in 50 mM Na-acetate (pH 5.5), and acetylated with 10 µl of mixture of triethylamine and acetic anhydride (2:1 vol:vol). After acetylation, cAMP antiserum (100 µl) is added from a stock solution (1:4000) made in PBS (pH 7.4), 5 mM EDTA and 1% normal rabbit serum. The tracer is diluted in PBS (pH 7.4) with 0.1% BSA, and added (20,000 cpm/tube). The assay is incubated at 4° C. overnight. The bound tracer is precipitated by adding 100 µl of goat anti-rabbit antiserum (1:20 in PBS) and 1 ml of 7% polyethyleneglycol (MW 5000-6000), centrifuging at 2000 rpm for 30 min. at 4° C. The supernatant is removed and the bound radioactivity is counted in a gamma-counter (Micromedic). To compute the cAMP data, logit calculations were performed in Excel spreadsheets. Typically, the assay sensitivity is 0.1 fmol/tube, and the standard concentration that displaces 50% of tracer is 5 fmol/tube.

Binding Assays

Binding reactions were performed with stably transfected HKRK-B7 cells in 24-well plates. Cells were rinsed with 0.5 mL of binding buffer (50 mM Tris-HCl, 100 mM NaCl, 5 mM KCl, 2 mM CaCl$_2$, 5% heat-inactivated horse serum, 0.5% fetal bovine serum, adjusted to pH 7.7 with HCl), and treated successively with 100 µL binding buffer, 100 µL of binding buffer containing various amounts of unlabeled competitor ligand, and 100 µL of binding buffer containing ca. 100,000 cpm of $^{125}$I-rPTH(1-34) (ca. 26 fmol). Incubations (final volume=300 µL) were at 15° C. for 4 h. Cells were then placed on ice, the binding medium was removed, and the monolayer was rinsed three times with 0.5 mL of cold binding buffer. The cells were subsequently lysed with 0.5 mL 5N NaOH and counted for radioactivity. The non-specific binding for each experiment was determined by competition with a 1 µM dose of unlabeled rPTH(1-34). The maximum specific binding ($B_0$) was the total radioactivity bound in the absence of unlabeled PTH ligand, corrected for nonspecific binding. Binding $IC_{50}$ values were determined using nonlinear regression (see below).

Data Calculation

All calculations were performed using Microsoft Excel. Nonlinear regression analysis of cAMP stimulation data was performed using parameters, defined as the Minimum, Maximum, $E_{max}$, midpoint (EC50, and slope of the response curve. The predicted response ($y_p$) for a given dose (x) of peptide was calculated using the following equation: $y_p$=Min+[(Max−Min)/(1+(EC50/x)$^{slope}$)]. The initial parameter values were estimated from the primary data, and the Excel "Solver function" was then used to vary the four parameters in order to minimize the differences between the predicted and actual responses (least-squares method) (Bowen, W., & Jerman, J., *Trends in Pharmacol. Sci.* 16:413-417 (1995)). The statistical significance between two data sets was determined using a one-tailed Student's t-test, assuming unequal variances for the two sets.

The amino acid substitutions in PTH(1-14) were discovered in a screen of 137 synthetic PTH(1-14) analogs that each had a single substitution. The substitutions were chosen by a "type-substitution" strategy in which at least one of each type of the 20 natural amino acids, and at least one D enantiomer, was introduced at each position in the 1-14 sequence. Each of the resulting peptides was examined for the ability to stimulate cAMP formation in a single-dose analysis in HKRK-B7 cells.

As shown in FIG. 1, most substitutions, particularly in the (1-9) segment, resulted in peptides that were inactive, but some led to peptides that were nearly as active as native PTH(1-14) and a few resulted in enhancing the signaling response (FIG. 1). Dose-response analysis indicated that these few single substitutions improved potency by several fold, relative to native PTH(1-14) (Not shown).

Example 2

Combined Substitutions of Amino Acids in PTH(1-14)

Several of the above activity-enhancing substitutions were first combined pair-wise to test for possible additive effects on activity. Each double mutant peptide (FIG. 2A) was more potent than either singly altered parent peptide (not shown). Likewise, each triple-mutant ligand was more potent than the corresponding double or single mutant ligand containing the same substitutions (FIG. 2B) (Compare FIG. 2A to 2B). Finally, the PTH(1-14) peptides containing four amino acid substitutions (peptides #1 and 3) or five amino acid substitutions (peptide # 2) were the most efficacious PTH(1-14) peptides tested and were 160 to 220 times more potent than native PTH(1-14) in HKRK-B7 cells (FIG. 2C; Table 2).

TABLE 2

| | Ligand-dependent cAMP responses in stable LLC-PK1 cells | | | | |
|---|---|---|---|---|---|
| | | EC50 * | | Emax | |
| | | Log M | µM | picomole/well | n |
| HKRK-B7 cells (hPTH-1 Receptor) control peptides | | | | | |
| | [Nle8, 21, Y34]rPTH(1-34) | −8.6 ± 0.1 | 0.0033 ± 0.0006 | 293 ± 29 | 10 |
| | [Y34]hPTH(1-34) | −8.4 | 0.0040 | 270 | 1 |
| | native rTPH(1-14) | −3.9 ± 0.0 | 133 ± 16.3 | 299 ± 27 | 10 |
| peptides of the invention | | | | | |
| #1 | [A3, A10, R11, A12]rPTH(1-14) | −6.1 ± 0.1 | 0.83 ± 0.22 | 264 ± 16 | 7 |
| #2 | [A3, A10, R11, A12, W14]rPTH(1-14) | −6.3 ± 0.1 | 0.6 ± 0.1 | 262 ± 9 | 3 |
| #3 | [A3, Q10, R11, A12]rPTH(1-14) | −6.1 ± 0.0 | 0.8 ± 0.1 | 235 ± 3 | 3 |
| #4 | [A3, A10, R11, A12]rPTH(1-13) | −5.6 ± 0.1 | 2.4 ± 0.3 | 239 ± 7 | 3 |
| #5 | [A3, A10, R11, A12]rPTH(1-12) | −5.0 ± 0.0 | 10.2 ± 0.2 | 238 ± 9 | 3 |
| #6 | [A3, A10, R11]rPTH(1-11) | −4.8 ± 0.0 | 17.1 ± 0.7 | 248 ± 13 | 3 |
| #7 | [A1, A3, A10, R11, A12, Y34]hPTH(1-34) | −8.8 | 0.0016 | 244 | 1 |
| LLC-P2R-22 cells (hPTH-2 Receptor) control peptides | | | | | |
| | [Nle8, 21, Y34]rPTH(1-34) | −8.4 ± 0.1 | 0.0044 ± 0.002 | 744 ± 48 | 3 |
| | native rPTH(1-14) | inactive | | | 3 |
| peptides of the invention | | | | | |
| #1 | [A3, A10, R11, A12]rPTH(1-14) | −3.9 ± 0.1 | 126 ± 23 | 292 ± 100 | 3 |
| #4 | [A3, A10, R11, A12]rPTH(1-13) | −4.0 | 106 | 501 | 1 |

TABLE 2-continued

Ligand-dependent cAMP responses in stable LLC-PK1 cells

|  |  | EC50 * | | Emax | |
|---|---|---|---|---|---|
|  |  | Log M | µM | picomole/well | n |
| #5 | [A3, A10, R11, A12]rPTH(1-12) | −3.5 | 342 | 501 | 1 |
| #6 | [A3, A10, R11]rPTH(1-11) | weakly active | | | 2 |
| #7 | [A1, A3, A10, R11, A12, Y34]rPTH(1-34) | −7.7 | 0.0192 | 677 | 1 |

Dose-response analysis for cAMP production was performed with the indicated peptides in LLC-PK1 cells stable transected with the human (h)PTH-1 receptor(HKRK-B7 cells) or the hPTH-2 receptor (P2R-22 cells), as described in the text.
native rPTH(1-14) - AVSEIQLMHNLGKH (SEQ. ID NO: 17).
native hPTH(1-14) -SVSEIQLMHNLGKH (SEQ. ID NO: 14).
native rPTH(1-34) - AVSEIQLMHNLGKHLASVERMQWLRKKLQDVHNF (SEQ. ID NO: 18).
native hPTH(1-34) -SVSEIQLMHNLGKHLNSMERVEWLRKKLQDVHNF (SEQ. ID NO: 19).
(See Potts et al., J. Endocrinol. 154: S15-S21, 1997)
* EC50 and corresponding Maximum response (Emax) values (mean ± SEM) were derived from four-parameter nonlinear regression equations used to curve-fit the data. In these calculations, Emax was constrained to within (±) 1standard deviation of the observed response for rPTH(1-34) at 100 nM.

Example 3

Substitutions of Amino Acids in Polypeptides Shorter than PTH(1-14)

Previously it was found that native rat PTH fragment analogs, PTH(1-13), PTH(1-12) PTH(1-11) PTH(1-10) and PTH(1-9) induced little or no cAMP response in HKRK-B7 cells (Luck, M. et al., *Mol. Endocrinol.* 13:670-680 (1999)). However, when all or some of the substitutions of Peptide #1 were transposed into these shorter peptides, as in peptides #4, #5, and #6, then signaling activity was readily observed (FIG. 3, Table 1). This is the first indication that a peptide as small as 11 amino acids (peptide # 6) can stimulate a cAMP response with the PTH-1 receptor; and even the analog [A3,Q10]rPTH(1-10) elicited some activity (FIG. 3). Note that for most of the shorter-length peptides in this study clear response maxima were not observed; estimates of the maximum responses (Emax) and corresponding EC50 values for these peptides were obtained from the nonlinear regression calculations used to curve-fit the data.

Example 4

Amino Acid Substitutions in PTH(1-34)

To determine if these substitutions could enhance the activity of PTH(1-34), the substitutions of Ser3→Ala, Asn10→Ala, Leu11→Arg and Gly12→Ala were introduced into the analog [Ala1,Tyr34]hPTH(1-34) to yield peptide #7. In HKRK-B7 cells this peptide was about 2-fold more potent than the two controls, rPTH(1-34) and hPTH(1-34) (Table 2). Competition binding studies performed in HKRK-B7 cells with $^{125}$I-rPTH(1-34) tracer radioligand and varying doses of peptide #7, indicated a commensurate ~2-fold improvement in binding affinity, as compared to rPTH(1-34) (FIG. 4).

Example 5

Stimulation of the PTH-2 Receptor

The PTH-2 receptor subtype selectively responds to PTH (1-34) and not PTHrP(1-34) (Usidin et al., *J. Biol. Chem.* 270:15455-15458 (1995)). Although, the physiological role of receptor subtype is not known it is widely expressed, particularly in the brain, aorta and pancreas (Usidin et al, *J. Biol. Chem.* 270:15455-15458 (1995)). Native PTH(1-14) did not stimulate the PTH-2 receptor expressed in LLC-PK1 cells; however, peptide #1 was active in these cells (FIG. 5, Table 1), although its potency was still four to five orders of magnitude weaker than that of PTH(1-34) (FIG. 5, Table 2). Thus, peptide #1 is a weak PTH-2 receptor agonist.

Example 6

PTH(−14) Stimulation of COS-7 Cells

Several of the PTH(1-14) analogs were examined for activity in COS-7 cells transiently transfected with the WT-hPTH-1 receptor (FIG. 6A, Table 3). As seen in HKRK-B7 cells, each analog was more potent than native PTH(1-14) in stimulating cAMP production. Similar improvements in potency were observed in COS-7 cells transfected with ΔNt (hDeINt), a truncated mutant hPTH-1 receptor that lacks most of the amino-terminal extracellular domain (FIG. 6B, Table 3). Importantly, peptide #7 was dramatically more potent than rPTH(1-34) or hPTH(1-34) in COS-7 cells expressing hΔNt (compare panels A and B of FIG. 6, Table 3). The inability to detect a large improvement in signaling potency of peptide #7 in studies performed with the intact PTH receptor

TABLE 3 cAMP stimulation with intact and truncated PTH-1 receptors in COS-7 cells

|  |  | EC50 | | Emax | |
|---|---|---|---|---|---|
|  |  | Log M | μM | picomole/well | n |
| WT hPTH-1 receptor control peptides | | | | | |
|  | [Nle8, 21, Y34]rPTH(1-34) | −9.2 ± 0.2 | 0.0007 ± 0.00023 | 226 ± 31 | 3 |
|  | [Y34]hPTH(1-34) | −9.3 ± 0.1 | 0.0005 ± 0.0001 | 226 ± 30 | 3 |
|  | native rTPH(1-14) | −3.8 ± 0.1 | 151.8 ± 35.2 | 221 ± 22 | 3 |
| peptides of the invention | | | | | |
| #1 | [A3, A10, R11, A12]rPTH(1-14) | −6.0 ± 0.1 | 4.66 ± 1.35 | 243 ± 63 | 3 |
| #6 | [A3, A10, R11]rPTH(1-11) | −4.6 ± 0.3 | 29.1 ± 15.3 | 238 ± 20 | 3 |
| #7 | [A1, A3, A10, R11, A12, Y34]hPTH(1-34) | −3.5 ± 0.2 | 313 ± 121 | 222 ± 31 | 3 |
| hDeINt control peptides | | | | | |
|  | [Nle8, 21, Y34]rPTH(1-34) | −5.3 ± 0.1 | 4.66 ± 1.35 | 243 ± 63 | 3 |
|  | [Y34]hPTH(1-34) | −4.6 ± 0.3 | 29.1 ± 15.3 | 238 ± 20 | 3 |
|  | native rPTH(1-14) | −3.5 ± 0.2 | 313 ± 121 | 222 ± 31 | 3 |
| peptides of the invention | | | | | |
| #1 | [A3, A10, R11, A12]rPTH(1-14) | −5.7 ± 0.2 | 2.37 ± 1.06 | 250 ± 61 | 3 |
| #6 | [A3, A10, R11]rPTH(1-11) | −4.6 ± 0.3 | 27.0 ± 12.9 | 243 ± 63 | 3 |
| #7 | [A1, A3, A10, R11, A12, Y34]rPTH(1-34) | −6.6 ± 0.3 | 0.28 ± 0.16 | 251 ± 39 | 3 |

Dose-response analysis for cAMP production was performed with the indicated peptides in COS-7 cells transiently transected with the WT hPTH-1 receptor or with the truncated receptor, hDeINt, as described in the text. EC50 andcorresponding maximum response (Emax) values (Mean ± SEM) were derived from four-parameter nonlinear regression equations used to curve-fit the data. In these calculations, Emax was constrained to within (±) 1 standarddeviation of the response observed for rPTH(1-34) at 100 nM for WT, and peptide #7 (20 μM) for hDeINt.

is not understood, but may reflect a limit in the ability to distinguish between highly efficacious agonists in these sensitive cell systems (Colquhoun, D. *Br. J. Pharmacol.* 125:924-947 (1998)). These peptides, however, can be distinguished with hΔNt, a cell/receptor system that is inherently much weaker than that in which intact PTH receptors are overexpressed. In any case, the results with hΔNt confirm that peptide #7 is indeed more potent than hPTH(1-34) or rPTH(1-34), and demonstrate that relative levels of efficacy and potency between analogs may vary depending on the pharmacological system employed.

None of the peptides reported here induced a cAMP response in non-transfected LLC-PK1 cells or in non-transfected COS-7 cells (data not shown) indicating that the observed effects were due to specific interactions with the PTH-1 receptor.

Example 7

Stimulation of ROS-17/2.8 and SAOS Cells by PTH(1-14) Derivatives

The key peptides of this study were tested for activity in two cell lines that were established directly from osteoblasts, the primary bone-building cell in vertebrates. These cell lines, ROS 17/2.8 (33) and SAOS-2, have been widely used in the PTH field for investigating effects of PTH analogs on bone cells. The responses observed for the peptides in these cells closely paralleled the responses observed in the cells transiently or stably transfected with the PTH-1 receptor (FIGS. 7A and B, Table 4).

TABLE 4

Ligand-dependent cAMP responses in osteoblast cells

|  |  | EC50 | | Emax | |
|---|---|---|---|---|---|
|  |  | Log M | μM | picomole/well | n |
| ROS 17/2.8 control peptides | | | | | |
|  | [Nle8, 21, Y34]rPTH(1-34) | −9.5 ± 0.14 | 0.0003 ± 1E−04 | 364 ± 6 | 2 |
|  | [Y34]hPTH(1-34) | −9.6 ± 0.00 | 0.0003 ± 3E−06 | 340 ± 55 | 2 |
|  | native rTPH(1-14) | −3.4 ± 0.11 | 449 ± 117 | 376 ± 23 | 2 |
| peptides of the invention | | | | | |
| #1 | [A3, A10, R11, A12]rPTH(1-14) | −5.2 ± 0.29 | 7.3 ± 4 | 395 ± 1 | 2 |
| #2 | [A3, A10, R11, A12, W14]rPTH(1-14) | −5.5 | 3.4 | 382 | 1 |
| #6 | [A3, A10, R11]rPTH(1-11) | −3.9 ± 0.35 | 133 ± 96 | 377 ± 23 | 2 |

TABLE 4-continued

Ligand-dependent cAMP responses in osteoblast cells

| | EC50 | | Emax | |
|---|---|---|---|---|
| | Log M | µM | picomole/well | n |
| #7 [A1, A3, A10, R11, A12, Y34]hPTH(1-34) SAOS-2 cells | −9.6 ± 0.02 | 0.0002 ± 1E−05 | 395 ± 1 | 2 |
| control peptides | | | | |
| [Nle8, 21, Y34]rPTH(1-34) | −9.75 ± 0.01 | 0.00018 ± 6E−06 | 272 ± 33 | 2 |
| [Y34]hPTH(1-34) | −9.28 | 0.00052 | 307 | 1 |
| native rPTH(1-14) | barely active | | | 2 |
| peptides of the invention | | | | |
| #1 [A3, A10, R11, A12]rPTH(1-14) | 12.7 | −4.9 | 331 | 1 |
| #6 [A3, A10, R11]rPTH(1-11) | 94.67 ± 79.54 | −4.12 ± 0.42 | 235 ± 7 | 2 |
| #7 [A1, A3, A10, R11, A12, Y34]rPTH(1-34) | 0.00011 ± 2E−05 | −9.95 ± 0.07 | 272 ± 33 | 2 |

Dose-response analysis for cAMP production was performed with the indicated peptides in the osteoblastic cell lines, ROS 17/2.8 and SAOS-2, as described in the text.
EC50 and corresponding maximum response (Emax) values (Mean ± SEM) were derived from four-parameter non-linear regression equations used to curve-fit the data. In these calculations, Emax was constrained to within (±)1 standard deviation of the response observed for rPTH(1-34) (100 nM).

Summary of Examples 1-7

Analog activity was first assessed in LLC-PK-1 cell stably expressing the human hPTH-1 receptor. Most substitutions at the intolerant positions abolished cAMP-stimulating activity. In contrast, most substitutions at the tolerant positions were compatible with function, and some, (Ser$^3$-->Ala; Asn$^{10}$-->Gln, Asp, Ala; Leu$^{11}$-->Arg or Lys; Gly$^{12}$-->Ala or Arg; and His$^{14}$-->Trp or Phe) enhanced activity. PTH(1-14) analogs having various combinantion of the activity-enhancing substitution were then synthesized. Each of these analogs was more potent than native PTH(1-14), and the effects of the substitutions were additive. Thus, [A$^3$, A$^{10}$, R$^{11}$, A$^{12}$]rPTH(1-14)amide was the most active analog tests, and was 100-fold more potent than native PTH(1-14). The object of this invention is to provide further PTH analogs.

Native PTH(1-14) stimulated cAMP formation in COS-7 cells expressing a truncated PTH-1 receptor rP1R-ΔNt, that lacks most of the amino-terminal extracellular domain. Each of the above activity-enhancing substitutions improved PTH(1-14) activity with rP1R-Δnt.

Additionally, peptide #1 was active in cells expressing the PTH-2 receptor (Example 5) and was active in osteoblast cells (Example 7), along with peptides #2, 6 and 7. Furthermore, PTH(1-34) with key substitutions in the 1-14 region was more potent than control PTH(1-34) in several cell lines examined.

Thus, these amino acid modifications improve interactions, either directly or indirectly, to the membrane-spannin/extracellular loop region of the receptor. Structure-activity relationship studies of PTH(1-14) could lead to more potent, low molecular weight PTH-1 receptor agonists, as well as to new insights into the ligand-receptor interaction mechanism.

Example 8

Stimulation of Bone Growth

A nucleic acid encoding a PTH derivative such as for example, that of SEQ ID NO:1, is transferred into bone cells in situ. Techniques for accomplishing this are described in U.S. Pat. No. 5,763,416 (fully incorporated herein by reference.) These cells may then be used to stimulate progenitor cells and to promote bone growth, repair and regeneration in vivo. Gene transfer protocols for accomplishing this are known to those of skill in the art and may be used as necessary to accomplish the desired objective. The objectives of such a procedure include inter alia, treating various bone-related diseases and defects, such as preventing fractures, promoting fracture repair, use in connection with implants, and in treating osteoporosis and osteogenesis imperfecta.

Example 9

Methods of Treating Osteoporosis

Subcutaneous administration of PTH(1-34) in combination with oral estrogen treatment results in increases in bone density for postmenopausal osteoporosis. (Abstract #1019, 1999 American Society of Bone and Mineral Research Meeting, Sept. 30-Oct. 4, 1999). The PTH derivatives of the claimed invention should also be effective in this regard. The PTH polypeptide derivative is provided to the patient, either subcutaneously, parenterally or by nasal insufflation in sufficient amounts to decrease the bone loss due to osteoporosis. Subcutaneous administration of the PTH derivative may be administered as necessary, for example daily at 400 IU/day. Oral estrogen may complement administration of the PTH derivative, for example at 800 IU daily.

Methods of the invention also include administering a vector comprising DNA encoding a PTH polypeptide derivative. The vector is administered either ex vivo or in vivo and is provided in an amount sufficient to provide an effective level of PTH in the patient or to increase cAMP in cells having PTH receptors. An "effective" level is that level of PTH that is produced in a healthy patient or that level necessary to replace bone loss in the pateint in need of such replacement Alternatively DNA encoding the PTH derivative is introduced into a cultured cells using a retrovirus to create PTH-secreting cells. The PTH-secreting cells are then transplanted into a patient in need of such treatment to provide serum levels of the PTH derivative.

CONCLUSIONS

A new family of PTH analogs that are the smallest peptides known to be capable of activating the PTH-1 receptor is described. These peptides contain one or more of the following key substitutions: Ser3→Ala, Asn10→Ala or Gln; Leu11→Arg, Gly12→Ala and His14→Trp and range in size from PTH(1-14) to PTH(1-11). Even PTH(1-10) containing Ser3→Ala and Asn10→Ala or Gln is found to be active. These analogs were active in stimulating cAMP formation in bone-derived osteoblast cells. The potency of these peptides, and their small size indicate that they should be useful for treating bone diseases, such as osteoporosis.

A PTH(1-34) analog containing the same key amino acid substitutions (Peptide # 7) is more potent than rPTH(1-34) and hPTH(1-34). Peptide #7 should also have utility in treating osteoporosis, as it has already been shown that the weaker peptide, native hPTH(1-34), in combination with estrogen, has dramatic anabolic effects on bone in postmenopausal women (22).

The major determinants of receptor binding and cAMP signaling in PTH are thought to reside within the C-terminal and N-terminal portion of PTH(1-34), respectively. Consistent with this, it was recently shown that PTH(1-14) can stimulate a weak cAMP response in cells expressing high levels of PTH-1 receptors {$EC_{50}$~100 µM vs. ~3 nM for PTH(1-34)} (Luck, M. D> et al., *Mol. Endocrin.* 13:670-680, (1999)). To identify receptor-signaling determinants in PTH(1-14), and to potentially improve potency, 137 singly substituted PTH(1-14) analogs were functionally evaluated in LLC-PK1 cells stably expressing the hPTH-1 receptor were synthesized. Although most substitutions diminished or abolished cAMP stimulating activity, some (e.g. Ser3→Ala, Asn10→Ala; Leu11→Arg, Gly12→Ala and His14→Trp) enhanced activity 2-to 5-fold. These enhancing effects were additive, such that $[A^3,A^{10},R^{11},A^{12}]$rPTH(1-14)amide (Peptide #1) $[A^3,A^{10},R^{11},A^{12},W^{14}]$rPTH(1-14) amide (Peptide #2) were 160- and 220-fold more potent than native PTH(1-14), respectively. PTH(1-34), or PTH(1-11) analogs containing some or all of these substitutions exhibited enhanced potency, relative to the unmodified control peptide. Peptide #1 was 100-fold more potent than native PTH(1-14) when tested on a truncated hPTH-1 receptor lacking most of the amino-terminal domain. The results demonstrate that the (1-14) region of PTH contains a critical activation core domain that interacts with the transmembrane domain/extracellular loop region of the receptor, and that this interaction can be optimized to yield higher potency short peptide agonists.

All references mentioned herein are fully incorporated by reference into the disclosure.

Having now fully described the invention by way of illustration and example for purposes of clarity and understanding, it will be apparent to those of ordinary skill in the art that certain changes and modifications may be made in the disclosed embodiments., and such modifications are intended to be within the scope of the present invention.

What is claimed is:

1. An isolated nucleic acid molecule encoding a biologically active polypeptide consisting of the amino acid sequence AlaValAlaGluIleGlnLeuMetHisX01X02X03LysX04 (SEQ ID NO: 1), wherein:

X01 is Ala, Asp or Gln;
X02 is Leu, Arg or homoArg;
X03 is Arg or Ala; and
X04 is Phe or Trp;

and wherein said polypeptide binds to a Parathyroid hormone-1 (PTH-1) receptor.

2. A recombinant DNA molecule comprising: (1) an expression control region, said region operably linked to (2) the nucleotide molecule of claim 1.

3. A method of preparing a polypeptide, comprising introducing the recombinant DNA of claim 2 into a host cell and expressing the polypeptide encoded by said nucleic acid.

4. The recombinant DNA molecule of claim 2, wherein said control region includes a bacterial, viral, fungal or mammalian promoter.

5. A prokaryotic or eukaryotic isolated host cell containing the recombinant DNA molecule of claim 2.

6. The cell of claim 5 which is bacterial.

7. The cell of claim 5 which is a yeast cell or a mammalian cell.

8. A method for making a recombinant vector comprising inserting a nucleic acid molecule of claim 1 into a vector.

* * * * *

UNITED STATES PATENT AND TRADEMARK OFFICE
CERTIFICATE OF CORRECTION

PATENT NO. : 7,371,844 B2  
APPLICATION NO. : 11/176735  
DATED : May 13, 2008  
INVENTOR(S) : Gardella et al.

It is certified that error appears in the above-identified patent and that said Letters Patent is hereby corrected as shown below:

Title Page 3, OTHER PUBLICATIONS, Line 25, in Roe, E.B., et al., "Parathyroid Hormone...", replace "Osteoporposis" with --Osteoporosis--.

Column 2, Line 35, replace "Bilzikian" with --Bilezikian--.

Column 4, Line 67, replace "(1993))" with --(1993)).--.

Column 7, Line 7, replace "HPTH" with --hPTH--;

Line 48, replace "PTH(11-20), PTH(11-22" with --PTH(1-20), PTH(1-22)--.

Column 8, Line 8, replace "GluIleGLN" with --GluIleGln--;

Line 9, replace "LysFisLeu" with --LysHisLeu--;

Line 14, replace "ArgvalGlu" with --ArgValGlu--;

Line 16, replace "GluIleGln" with --GluIleGln--;

Line 66, replace "PTH(-32)" with --PTH(1-32)--.

Column 15, In the Caption under Table 1, Line 2, replace "algorithmof" with --algorithm of--;

In the Caption under Table 1, Line 3, replace "packageof" with --package of--.

Column 17, Line 25, replace "polydeoxribonucleotide" with --polydeoxyribonucleotide--.

Signed and Sealed this

Twenty-fourth Day of August, 2010

David J. Kappos  
*Director of the United States Patent and Trademark Office*

CERTIFICATE OF CORRECTION (continued)
U.S. Pat. No. 7,371,844 B2

Column 18, Line 43, replace "organsim" with --organism--.

Column 19, Line 57, replace "derivatiaves" with --derivatives--.

Column 26, Line 25, replace "somatitis" with --stomatitis--.

Column 35, Line 53, replace "pcDNA-1" with --pCDNA-1--.

Column 36, Line 29, replace "acetonitrille" with --acetonitrile--.

Column 41, Line 5, In the Caption under Table 3, Line 3, replace "andcorresponding" with --and corresponding-- and replace "standarddeviation" with --standard deviation--.

Column 43, Line 33, replace "combinantion" with --combination--;

Line 52, replace "membrane-spannin/" with --membrane-spanning-- .

Column 44, Line 53, replace "pateint" with --patient--.

SEQUENCE LISTING

```
<160> NUMBER OF SEQ ID NOS: 31

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala, Asp or Gln
<220> FEATURE:
<221> NAME/KEY: UNSURE
<222> LOCATION: (11)
<223> OTHER INFORMATION: Xaa can be Leu, Arg, or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp

<400> SEQUENCE: 1

Ala Val Ala Glu Ile Gln Leu Met His Xaa Xaa Xaa Lys Xaa
  1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide
```

```
<220> FEATURE:
<221> NAME/KEY: UNSURE
<222> LOCATION: (10)
<223> OTHER INFORMATION: Xaa can be Ala or Gln
<220> FEATURE:
<221> NAME/KEY: UNSURE
<222> LOCATION: (14)
<223> OTHER INFORMATION: Xaa can be Trp or His

<400> SEQUENCE: 2

Ala Val Ala Glu Ile Gln Leu Met His Xaa Arg Ala Lys Xaa
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 3

Ala Val Ala Glu Ile Gln Leu Met His Ala Arg Ala Lys His
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 4

Ala Val Ser Glu Ile Gln Leu Met His Asn Arg Gly Lys His
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 5

Ala Val Ser Glu Ile Gln Leu Met His Asn Arg Ala Lys His
 1               5                  10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 6

Ala Val Ala Glu Ile Gln Leu Met His Asn Arg Ala Lys His
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide
```

```
<400> SEQUENCE: 7

Ala Val Ala Glu Ile Gln Leu Met His Ala Arg Ala Lys Trp
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 8

Ala Val Ala Glu Ile Gln Leu Met His Gln Arg Ala Lys His
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 9

Ala Val Ala Glu Ile Gln Leu Met His Ala Arg Ala Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 10

Ala Val Ala Glu Ile Gln Leu Met His Ala Arg Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 11

Ala Val Ala Glu Ile Gln Leu Met His Ala Arg
1               5                   10

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 12

Ala Val Ala Glu Ile Gln Leu Met His Ala Arg Ala Lys His Leu Asn
1               5                   10                  15

Ser Met Glu Arg Val Glu Trp Leu Arg Lys Lys Leu Gln Asp Val His
            20                  25                  30

Asp Tyr
```

-continued

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 13

Ala Val Ser Glu Ile Gln Leu Met His Ala Arg Ala Lys His
 1               5                  10

<210> SEQ ID NO 14
<211> LENGTH: 14
<212> TYPE: PRT
<213> ORGANISM: Homo sapiens

<400> SEQUENCE: 14

Ser Val Ser Glu Ile Gln Leu Met His Asn Leu Gly Lys His
 1               5                  10

<210> SEQ ID NO 15
<211> LENGTH: 14
<212> TYPE: PRT
<213> ORGANISM: Homo sapiens

<400> SEQUENCE: 15

Ser Val Ser Glu Ile Gln Leu Met His Asn Leu Gly Lys His
 1               5                  10

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (34)
<223> OTHER INFORMATION: Xaa can be Phe or Tyr

<400> SEQUENCE: 16

Ala Val Ala Glu Ile Gln Leu Met His Xaa Xaa Xaa Lys Xaa Leu Asn
 1               5                  10                  15

Ser Met Glu Arg Val Glu Trp Leu Arg Lys Lys Leu Gln Asp Val His
             20                  25                  30

Asp Xaa

<210> SEQ ID NO 17
<211> LENGTH: 14

```
<212> TYPE: PRT
<213> ORGANISM: Rattus norvegicus

<400> SEQUENCE: 17

Ala Val Ser Glu Ile Gln Leu Met His Asn Leu Gly Lys His
1               5                   10

<210> SEQ ID NO 18
<211> LENGTH: 34
<212> TYPE: PRT
<213> ORGANISM: Rattus norvegicus

<400> SEQUENCE: 18

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 19
<211> LENGTH: 34
<212> TYPE: PRT
<213> ORGANISM: Homo sapiens

<400> SEQUENCE: 19

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 20

Ala Val Ala Glu Ile Gln Leu Met His Ala Arg Ala Lys His Leu Ala
1               5                   10                  15

Ser Val Glu Arg Met Gln Trp Leu Arg Lys Lys Leu Gln Asp Val His
            20                  25                  30

Asp Tyr

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
```

```
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (34)
<223> OTHER INFORMATION: Xaa can be Phe or Tyr

<400> SEQUENCE: 21

Ser Val Ala Glu Ile Gln Leu Met His Xaa Xaa Xaa Lys Xaa Leu Ala
1               5                   10                  15

Ser Val Glu Met Gln Glu Trp Leu Arg Lys Lys Leu Gln Asp Val His
            20                  25                  30

Asp Xaa

<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 22

Ala Val Ala Glu Ile Gln Leu Met His Ala Arg Ala Lys His Leu Asn
1               5                   10                  15

Ser Met Glu Arg Val Glu Trp Leu Arg Lys Lys Leu Gln Asp Val His
            20                  25                  30

Asp Tyr

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 23

Ala Val Ala Glu Ile Gln Leu Met His Ala Arg Ala Lys His Leu Ala
1               5                   10                  15

Ser Val Arg Arg Met Gln Trp Leu Arg Lys Lys Leu Gln Asp Val His
            20                  25                  30

Asp Tyr

<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: modified
      PTH peptide

<400> SEQUENCE: 24

Ala Val Ala Glu Ile Gln Leu Met His Ala Arg Ala Lys His Leu Asn
1               5                   10                  15

Ser Met Arg Arg Val Glu Trp Leu Arg Lys Lys Leu Gln Asp Val His
            20                  25                  30

Asp Tyr

<210> SEQ ID NO 25
<211> LENGTH: 20
```

```
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa can be Arg or Ala

<400> SEQUENCE: 25

Ala Val Ala Glu Ile Gln Leu Met His Xaa Xaa Xaa Lys Xaa Leu Asn
 1               5                  10                  15

Ser Met Xaa Arg
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa can be Arg or Ala

<400> SEQUENCE: 26

Ala Val Ala Glu Ile Gln Leu Met His Xaa Xaa Xaa Lys Xaa Leu Asn
 1               5                  10                  15

Ser Met Xaa Arg Val Glu
            20

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: modified
      PTH peptide
```

```
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa can be Arg or Ala

<400> SEQUENCE: 27

Ala Val Ala Glu Ile Gln Leu Met His Xaa Xaa Xaa Lys Xaa Leu Asn
  1               5                  10                  15

Ser Met Xaa Arg Val Glu Trp Leu
             20

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa can be Arg or Ala

<400> SEQUENCE: 28

Ala Val Ala Glu Ile Gln Leu Met His Xaa Xaa Xaa Lys Xaa Leu Asn
  1               5                  10                  15

Ser Met Xaa Arg Val Glu Trp Leu Arg Lys
             20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
```

```
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa can be Arg or Ala

<400> SEQUENCE: 29

Ala Val Ala Glu Ile Gln Leu Met His Xaa Xaa Xaa Lys Xaa Leu Asn
  1               5                  10                  15

Ser Met Xaa Arg Val Glu Trp Leu Arg Lys Lys Leu
             20                  25

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa canbe Arg or Ala

<400> SEQUENCE: 30

Ala Val Ala Glu Ile Gln Leu Met His Xaa Xaa Xaa Lys Xaa Leu Asn
  1               5                  10                  15

Ser Met Xaa Arg Val Glu Trp Leu Arg Lys Lys Leu Gln Asp
             20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: modified
      PTH peptide
<220> FEATURE:
<221> NAME/KEY: UNSURE
<222> LOCATION: (10)
<223> OTHER INFORMATION: Xaa can be Ala or Asp
<220> FEATURE:
<221> NAME/KEY: UNSURE
<222> LOCATION: (11)
<223> OTHER INFORMATION: Xaa can be Leu, Arg or homoArg
<220> FEATURE:
<221> NAME/KEY: UNSURE
```

```
<222> LOCATION: (12)
<223> OTHER INFORMATION: Xaa can be Arg or Ala
<220> FEATURE:
<221> NAME/KEY: UNSURE
<222> LOCATION: (14)
<223> OTHER INFORMATION: Xaa can be Phe or Trp
<220> FEATURE:
<221> NAME/KEY: UNSURE
<222> LOCATION: (19)
<223> OTHER INFORMATION: Xaa can be Arg or Ala

<400> SEQUENCE: 31

Ala Val Ala Glu Ile Gln Leu Met His Xaa Xaa Xaa Lys Xaa Leu Asn
 1               5                  10                  15

Ser Met Xaa Arg Val Glu Trp Leu Arg Lys Lys Leu Gln Asp Val His
            20                  25                  30
```